US012582676B2

(12) United States Patent
Chick et al.

(10) Patent No.: US 12,582,676 B2
(45) Date of Patent: Mar. 24, 2026

(54) HYDROGEL PARTICLE ENCAPSULATED VIABLE CELLS FOR IN VIVO REGENERATIVE TREATMENT

(71) Applicant: CellDrop Biosciences, Inc., Laramie, WY (US)

(72) Inventors: Wallace Chick, Greenwood Village, CO (US); Benjamin Noren, Laramie, WY (US)

(73) Assignee: CellDrop Biosciences, Inc., Laramie, WY (US)

( * ) Notice: Subject to any disclaimer, the term of this patent is extended or adjusted under 35 U.S.C. 154(b) by 43 days.

(21) Appl. No.: 18/354,636

(22) Filed: Jul. 18, 2023

(65) Prior Publication Data

US 2024/0024364 A1 Jan. 25, 2024

Related U.S. Application Data

(60) Provisional application No. 63/390,501, filed on Jul. 19, 2022.

(51) Int. Cl.

| | |
|---|---|
| *A61K 35/28* | (2015.01) |
| *A61K 9/06* | (2006.01) |
| *A61K 47/10* | (2017.01) |
| *A61P 19/04* | (2006.01) |
| *B01J 13/18* | (2006.01) |
| *C08J 3/075* | (2006.01) |
| *C08J 3/28* | (2006.01) |
| *C12N 5/071* | (2010.01) |

(52) U.S. Cl.
CPC ............... *A61K 35/28* (2013.01); *A61K 9/06* (2013.01); *A61K 47/10* (2013.01); *A61P 19/04* (2018.01); *B01J 13/18* (2013.01); *C08J 3/075* (2013.01); *C08J 3/28* (2013.01); *C12N 5/0602* (2013.01); *C08J 2300/14* (2013.01); *C12N 2533/30* (2013.01)

(58) Field of Classification Search
None
See application file for complete search history.

(56) References Cited

U.S. PATENT DOCUMENTS

| | | | |
|---|---|---|---|
| 9,642,814 B2 | 5/2017 | Ramachandran et al. | |
| 10,912,860 B2 | 2/2021 | Griffin et al. | |
| 2004/0038356 A1 | 2/2004 | Pertoft et al. | |
| 2007/0134209 A1 | 6/2007 | Oakey | |
| 2012/0087983 A1 | 4/2012 | Katz et al. | |
| 2012/0265297 A1 | 10/2012 | Altman et al. | |
| 2016/0258856 A1 | 9/2016 | Kim et al. | |
| 2016/0362655 A1 | 12/2016 | Demirci et al. | |
| 2017/0145169 A1 | 5/2017 | Oakey et al. | |
| 2022/0064624 A1 | 3/2022 | Noren et al. | |
| 2022/0233454 A1 | 7/2022 | Ott et al. | |

FOREIGN PATENT DOCUMENTS

| | | |
|---|---|---|
| CN | 106459896 A | 2/2017 |
| WO | 2021232013 A1 | 11/2021 |
| WO | 2022125762 A1 | 6/2022 |

OTHER PUBLICATIONS

Zhao et al (Injectable Stem Cell-Laden Photocrosslinkable Microspheres Fabricated Using Microfluidics for Rapid Generation of Osteogenic Tissue Constructs. Adv. Funct. Mater. 2016, 26, 2809-2819) (Year: 2016).*

Lin et al (Facile synthesis of rapidly degrading PEG-based thiol-norbornene hydrogels. ACS Macro Lett. Mar. 16, 2021; 10(3): 341-345) (Year: 2021).*

Feng et al (Microgel assembly: Fabrication, characteristics and application in tissue engineering and regenerative medicine. Bioactive Materials 9 (2022) 105-119, available online Jul. 23, 2021) (Year: 2021).*

Asanbe, Md et al., "Innovative 3D Collagen Microsphere Scaffold (MSS) Promotes Robust Cellular Invasion," Plastic Surgery 2014, Abstract Supplement, p. 28.

International Search Report and Written Opinion dated Jan. 23, 2024 for International Application No. PCT/US2023/070466.

Density Gradient Media. OptiPrep™ The ideal density gradient medium for isolation of cells, 1-8, Feb. 1, 2022, [retrieved on Aug. 9, 2023]. Retrieved from the Internet. https://iccb.med.harvard.edu/files/iccb/files/optiprep.pdf.

Ding et al., Reversible methane storage in porous hydrogel supported clathrates. Pharm Res. 96(7): 1-24, Mar. 29, 2013 [retrieved on Aug. 9, 2023]. Retrieved from the Internet.

International Search Report and Written Opinion dated Sep. 25, 2023 for International Application No. PCT/US2023/026823.

Shin et al., Centrifuge-based Step Emulsification Device for Simple and Fast Generation of Monodisperse Picoliter Droplets. Sensors and Actuators B: Chemical 301: 1-22, Sep. 23, 2019 [retrieved on Aug. 9, 2023]. Retrieved from the Internet.

Tao, et al., Fabrication of antibacterial sericin based hydrogel as an injectable and mouldable wound dressing, 1-9, Oct. 8, 2020, [retrieved on Aug. 9, 2023]. Retrieved from the Internet.

Tiemeijer et al., Hydrogels for Single-Cell Microgel Production: Recent Advances and Applications. Front. Bioeng. Biotechnol. 10: 1-19, Jun. 17, 2022 [retrieved on Aug. 9, 2023].Retrieved from the Internet.

(Continued)

*Primary Examiner* — Jake M Vu

(74) *Attorney, Agent, or Firm* — Avek IP, LLC

(57) ABSTRACT

A composition for tendon and ligament regeneration includes a biologically compatible hydrogel suspension having spherical droplets. The spherical droplets have a diameter of about 100 μm to about 300 μm and a plurality of cells. The cells include marrow-derived mesenchymal stem cells (MSCs) with an average viability of about 90% or greater and cells that retain their stemness. A method for tendon and ligament regeneration includes forming the composition, purifying the composition, retrieving the composition, and administering the composition via injection into an injury site of injured tissue.

6 Claims, 17 Drawing Sheets

(56)  References Cited

OTHER PUBLICATIONS

English translation of Search Report issued Mar. 4, 2024 in related Taiwan application No. 112126818.

Office Action issued Mar. 4, 2024 in related Taiwan application No. 112126818.

Brooks EA, Jansen LE, Gencoglu MF, Yurkevicz AM, Peyton SR. Complementary, Semiautomated Methods for Creating Multidimensional PEG-Based Biomaterials. ACS Biomater Sci Eng. 2018;4(2): 707-718. doi: 10.1021/ acsbiomaterials.7b00737 (Year: 2018).

CryoProTM User Guide Hampton Research (p. 1-7) (Year: 2021).

Martinez CJ, Kim JW, Ye C, et al. A microfluidic approach to encapsulate living cells in uniform alginate hydrogel microparticles. Macromol Biosci. 2012;12(7):946-951. doi: 10.1002/mabi. 201100351 (Year: 2012).

Tasoglu S, Yu CH, Gungordu HI, Guven S, Vural T, Demirci U. Guided and magnetic self-assembly of tunable magnetoceptive gels. Nat Commun. 2014;5:4702. Published Sep. 1, 2014. doi:10.1038/ ncomms5702 (Year: 2014).

* cited by examiner

100

COMBINE HYDROGEL MATERIALS — 110

↓

MIX HYDROGEL MATERIALS — 120

↓

POLYMERIZE HYDROGEL — 130

↓

REMOVE SUSPENSION MEDIA — 140

↓

WASH HYDROGEL PARTICLES — 150

↓

RESUSPEND HYDROGEL PARTICLES — 160

HYDROGEL PARTICLE RECOVERY

200

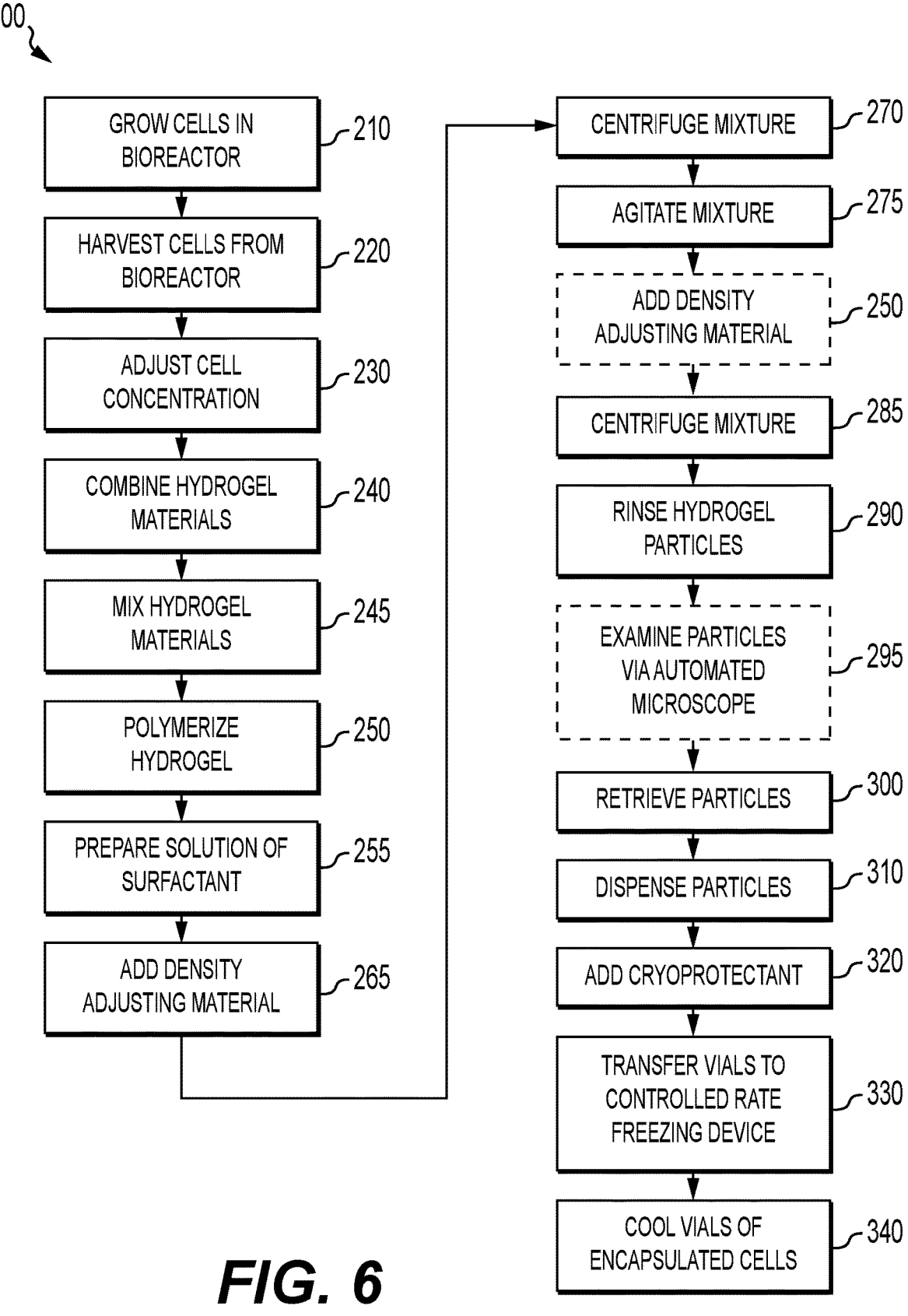

GROW CELLS IN BIOREACTOR — 210

HARVEST CELLS FROM BIOREACTOR — 220

ADJUST CELL CONCENTRATION — 230

COMBINE HYDROGEL MATERIALS — 240

MIX HYDROGEL MATERIALS — 245

POLYMERIZE HYDROGEL — 250

PREPARE SOLUTION OF SURFACTANT — 255

ADD DENSITY ADJUSTING MATERIAL — 265

CENTRIFUGE MIXTURE — 270

AGITATE MIXTURE — 275

ADD DENSITY ADJUSTING MATERIAL — 250

CENTRIFUGE MIXTURE — 285

RINSE HYDROGEL PARTICLES — 290

EXAMINE PARTICLES VIA AUTOMATED MICROSCOPE — 295

RETRIEVE PARTICLES — 300

DISPENSE PARTICLES — 310

ADD CRYOPROTECTANT — 320

TRANSFER VIALS TO CONTROLLED RATE FREEZING DEVICE — 330

COOL VIALS OF ENCAPSULATED CELLS — 340

*FIG. 6*

BONAR SCORING FOR AREA OF GREATEST PATHOLOGY

PERCENT HEALTHY TISSUE IN ACHILLES TENDON 28 DAYS AFTER TREATMENT

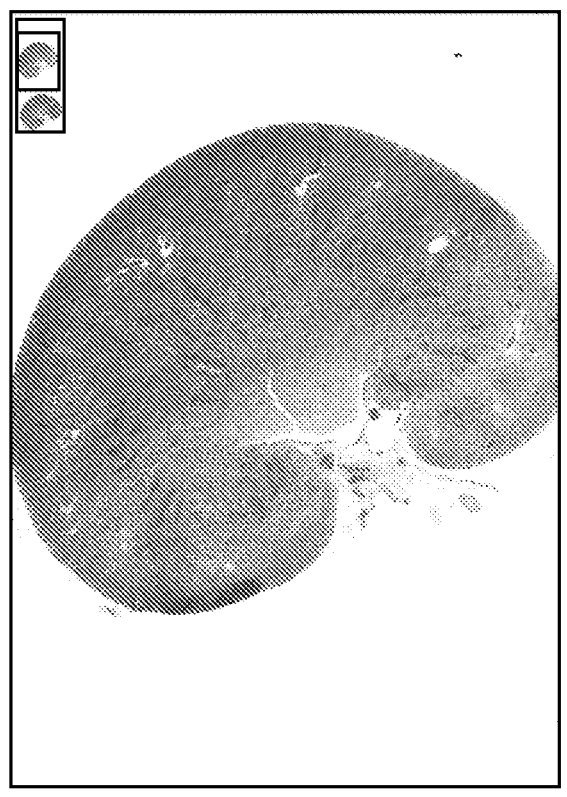
*FIG. 20B*
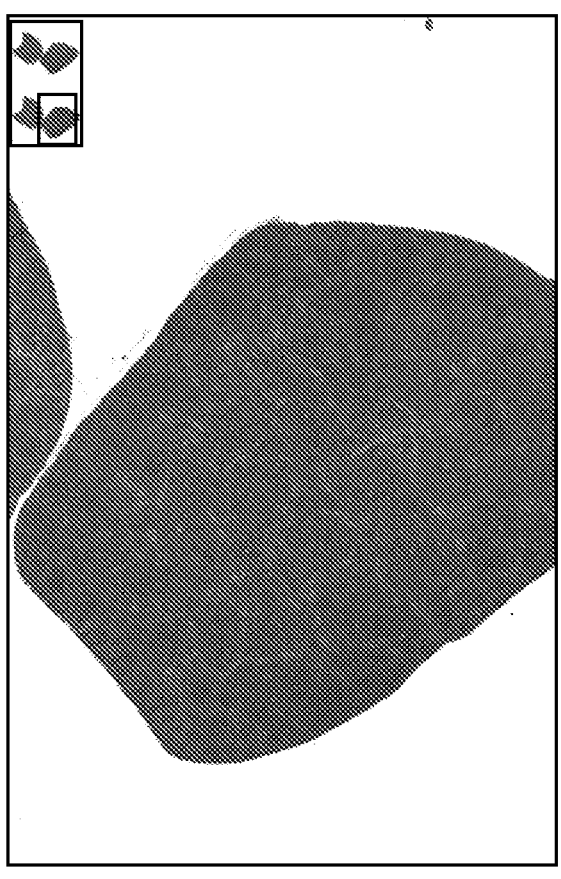
*FIG. 20A*

HYDROGEL PARTICLE ENCAPSULATED VIABLE CELLS FOR IN VIVO REGENERATIVE TREATMENT

CROSS-REFERENCE TO RELATED APPLICATIONS

This application claims the benefit of priority of U.S. Provisional Patent Application No. 63/390,501 entitled Particle Encapsulation and Suspension Media Removal and filed on Jul. 19, 2022, the disclosure of which is herein incorporated by reference in its entirety.

STATEMENT REGARDING FEDERALLY SPONSORED RESEARCH OR DEVELOPMENT

This invention was made with government support under Award No. 2038460 awarded by the National Science Foundation. The government has certain rights in the invention.

BACKGROUND

1. Field

Embodiments of the invention relate to hydrogel particle production methods. More specifically, embodiments of the invention relate to removal of suspension media from hydrogel particles and methods and compositions for in vivo administering of cells contained in the hydrogel particles.

2. Related Art

A variety of hydrogel particle production methods are known. For example, U.S. Patent Application Publication No. 2007/0134209 to Oakey discloses methods for producing a cellular matrix for tissue self-assembly in which living cells are encapsulated in a primary encapsulant followed by encapsulation in a secondary encapsulant that is polymerized. U.S. Patent Application Publication No. 2017/0145169 to Oakey et al. discloses methods of using microfluidics for the oxygen-controlled generation of microparticles and hydrogels for biological applications.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

In an embodiment, a composition for orthopedic tissue rejuvenation includes a biologically compatible hydrogel suspension having spherical droplets, wherein the spherical droplets include: a diameter of about 100 μm to about 300 μm; a plurality of cells encapsulated within the spherical droplets, wherein the cells have an average viability of about 90% or greater.

In another embodiment, a composition for tendon and ligament regeneration includes: a biologically compatible hydrogel suspension having spherical droplets, wherein the spherical droplets include: a diameter of about 100 μm to about 300 μm; a plurality of cells, wherein the cells include:

marrow-derived mesenchymal stem cells (MSCs); an average viability of about 90% or greater; and the cells retain their stemness.

In yet another embodiment, a method for tendon and ligament regeneration includes: forming a composition, wherein the composition includes hydrogel particles with encapsulated viable cells, the step of forming including: combining hydrogel materials in a container, the hydrogel materials including a hydrogel polymer, a linker, a viable cell suspension, and a suspension media; mixing the hydrogel materials to form a hydrogel-suspension media mixture, wherein mixing includes shaking the container until the hydrogel materials are substantially mixed without substantially decreasing viability of the viable cells; and polymerizing the hydrogel materials to form hydrogel particles having encapsulated viable cells; purifying the composition, including: adding a density adjusting material; adding cargo-compatible solution wherein the cargo-compatible solution includes a cargo-compatible surfactant; centrifuging the hydrogel-suspension media mixture with the density adjusting material and cargo-compatible solution to form a three-phase solution including: 1) an upper phase including the hydrogel particles suspended within the cargo-compatible solution, 2) a middle phase including the density adjusting material, and 3) a lower phase including the suspension media; agitating the three-phase solution via mechanical agitation; centrifuging the three-phase solution; and retrieving the composition by collecting the upper phase such that the composition substantially lacks the suspension media; and administering the composition via injection into an injury site of injured animal tissue.

BRIEF DESCRIPTION OF THE DRAWING FIGURES

Embodiments of the invention are described in detail below with reference to the attached drawing figures, wherein:

FIG. 6 is a block diagram showing an exemplary automated encapsulation method, in an embodiment;

Figure 9A:
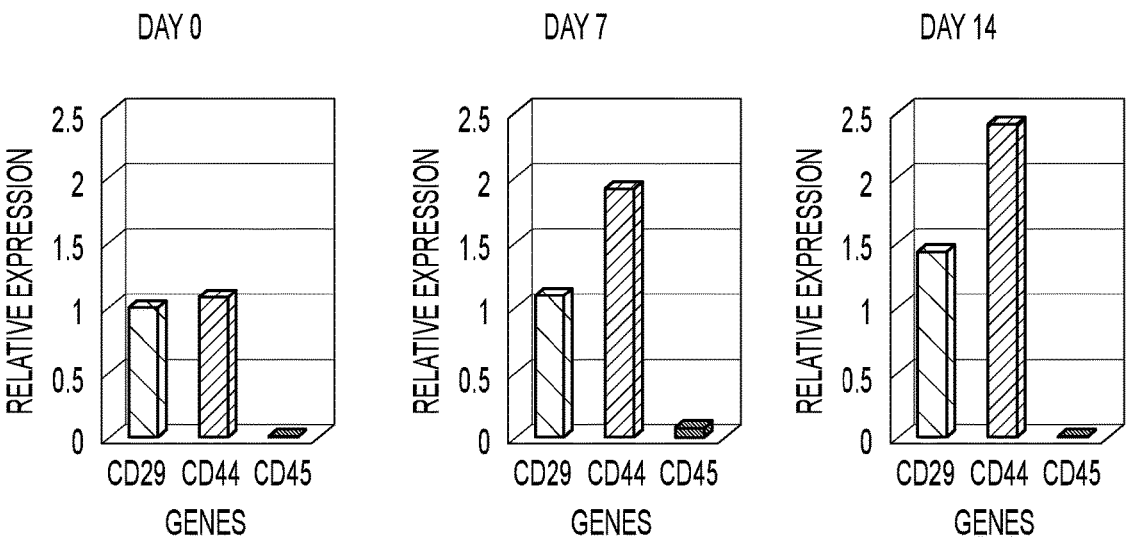
Figure 9B:
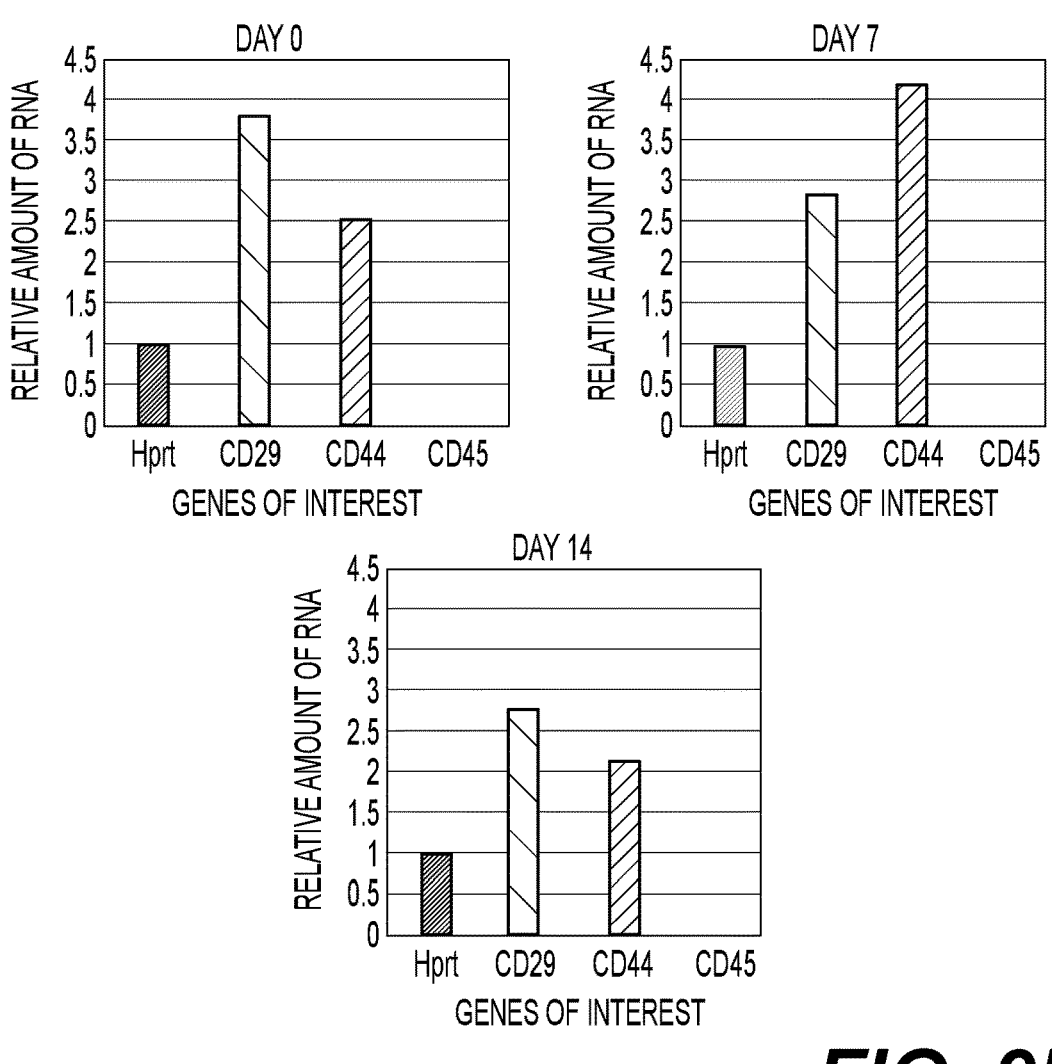
Figure 10:
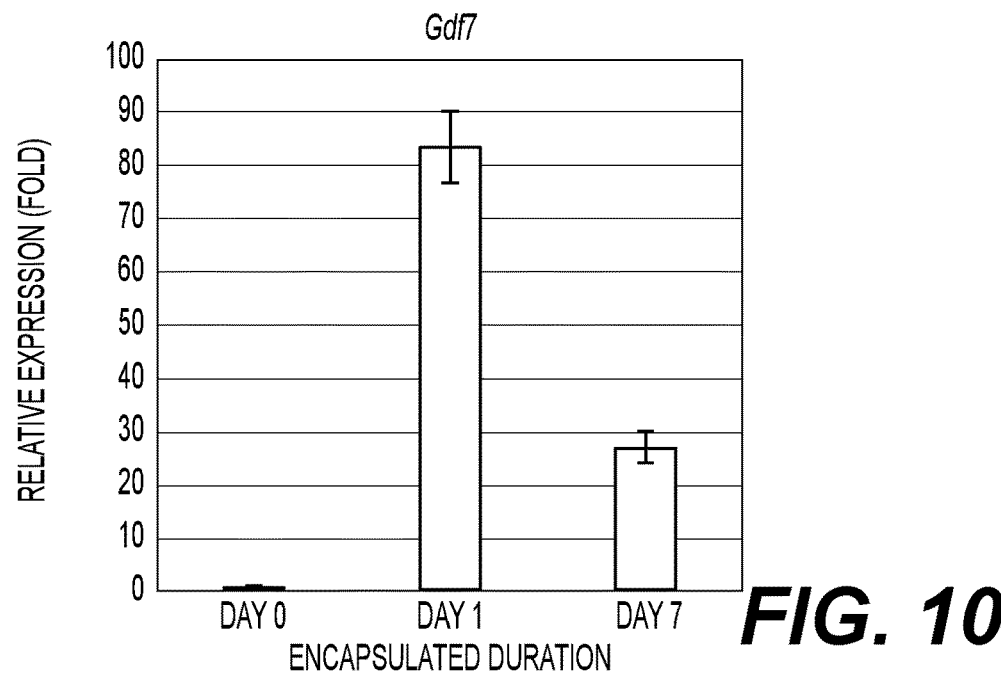
Figures 11A, 11B, 11C:
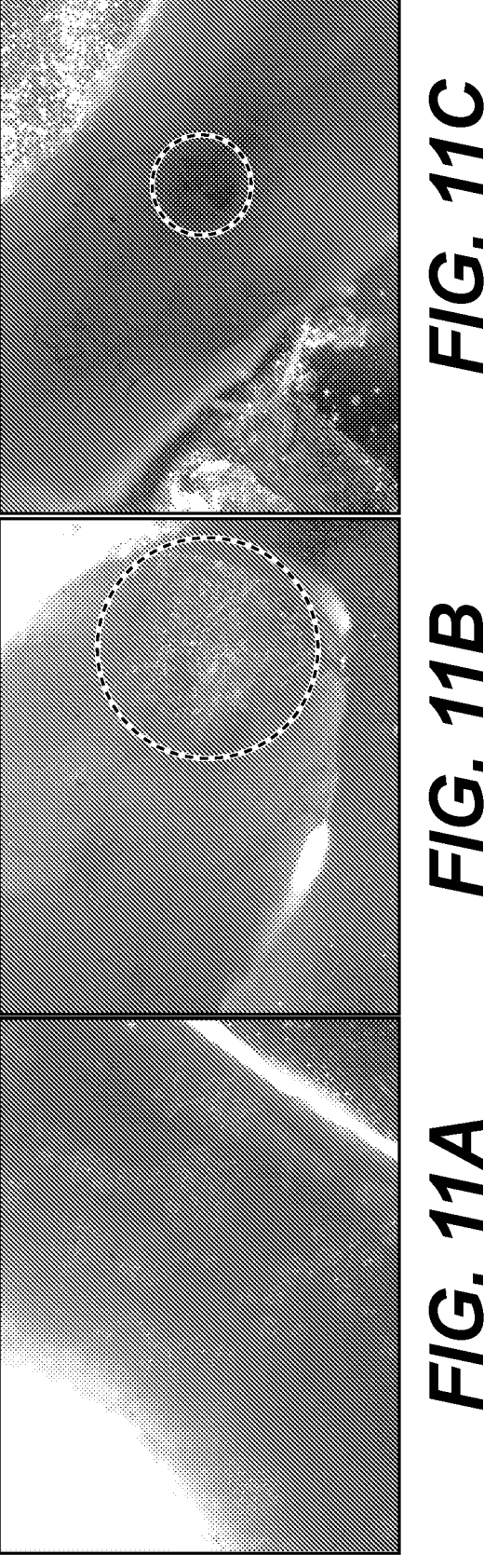
Figure 12:
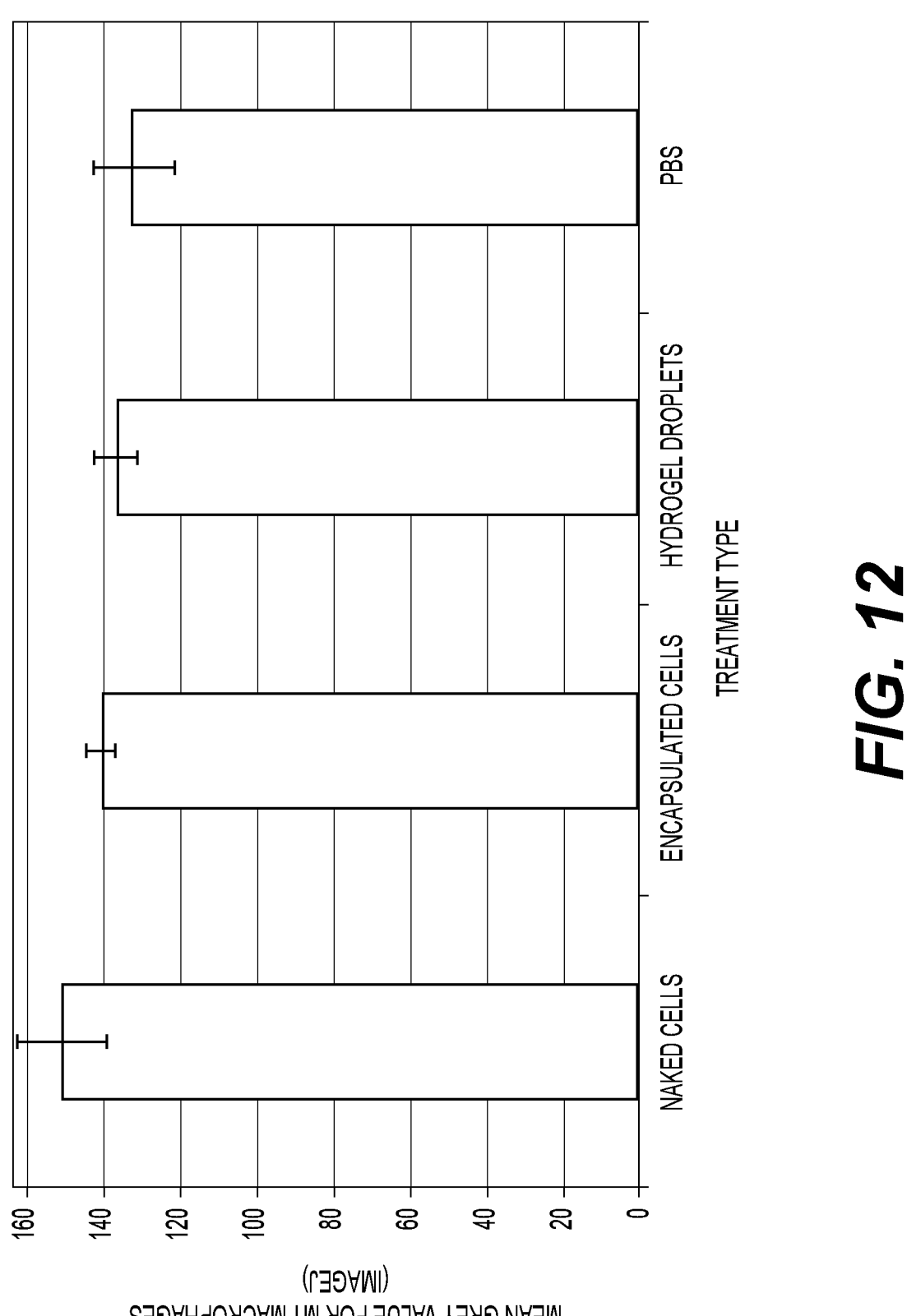
Figures 13A, 13B, 13C, 13D:
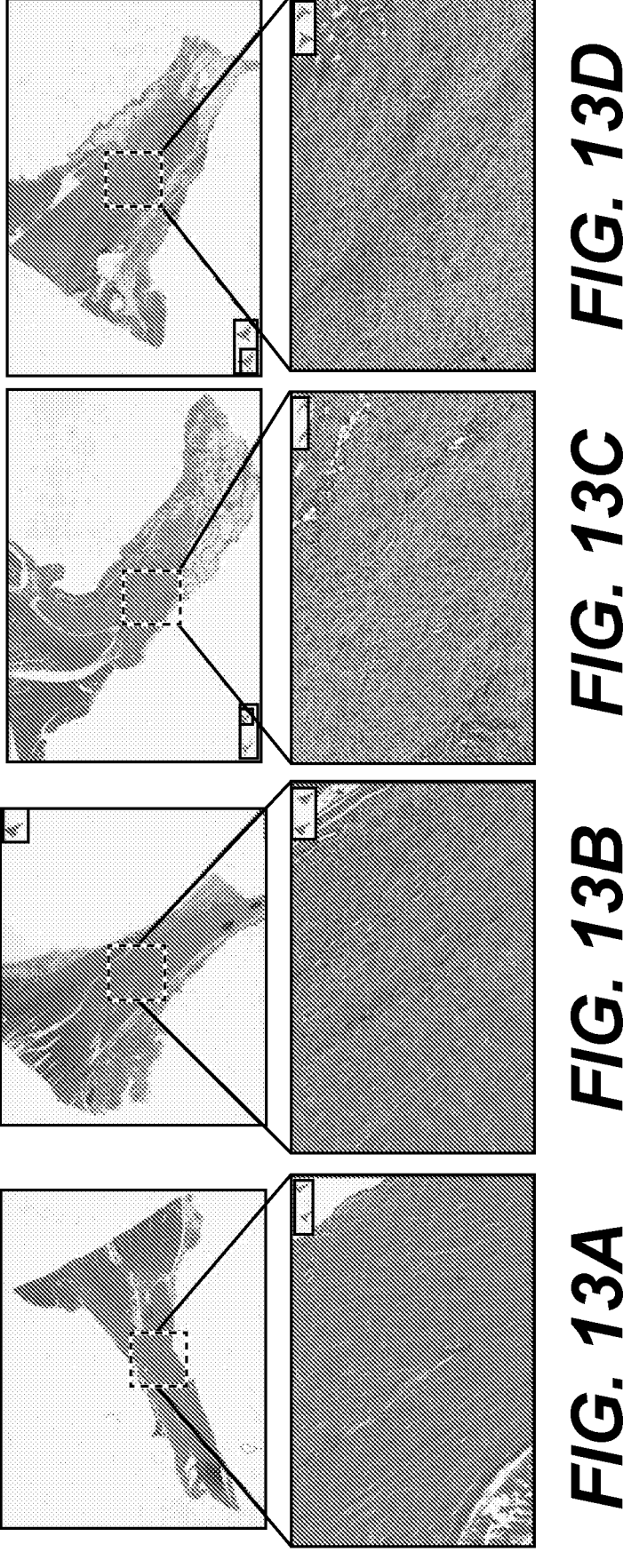
Figures 14A, 14B, 14C, 14D:
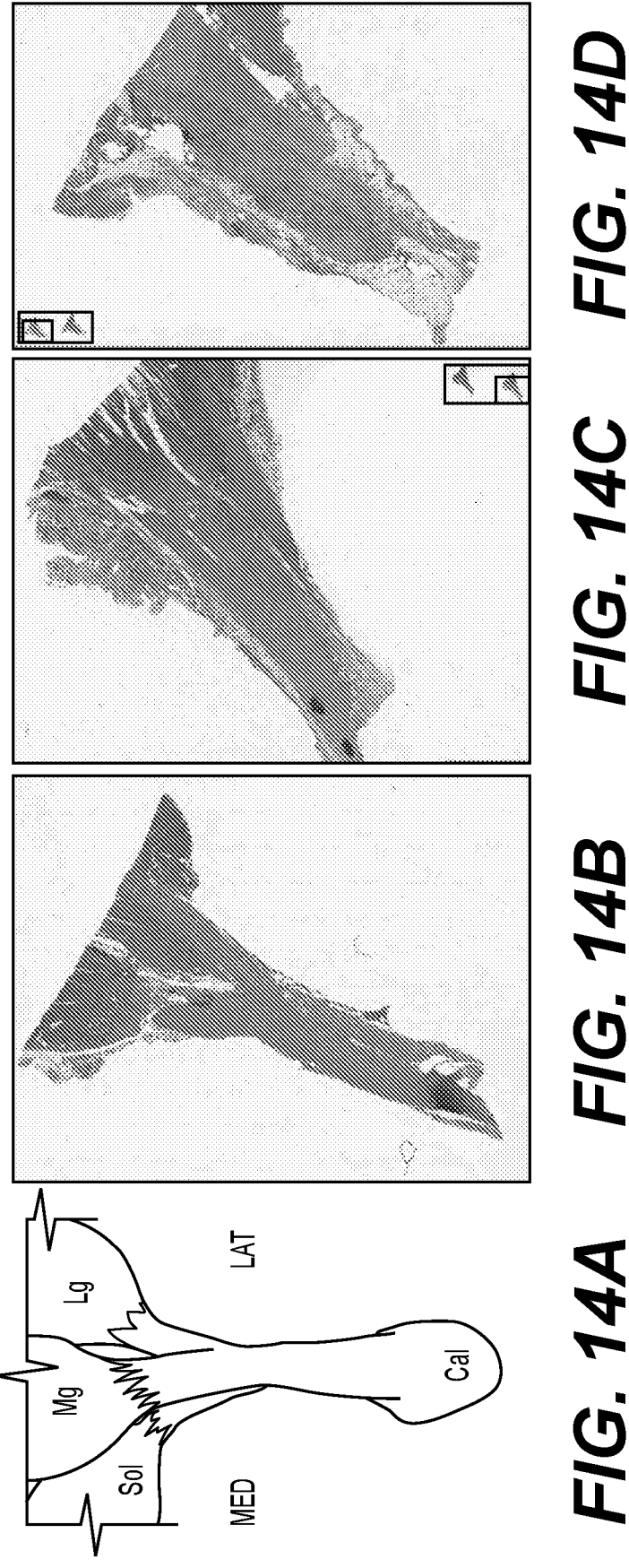
Figure 15:
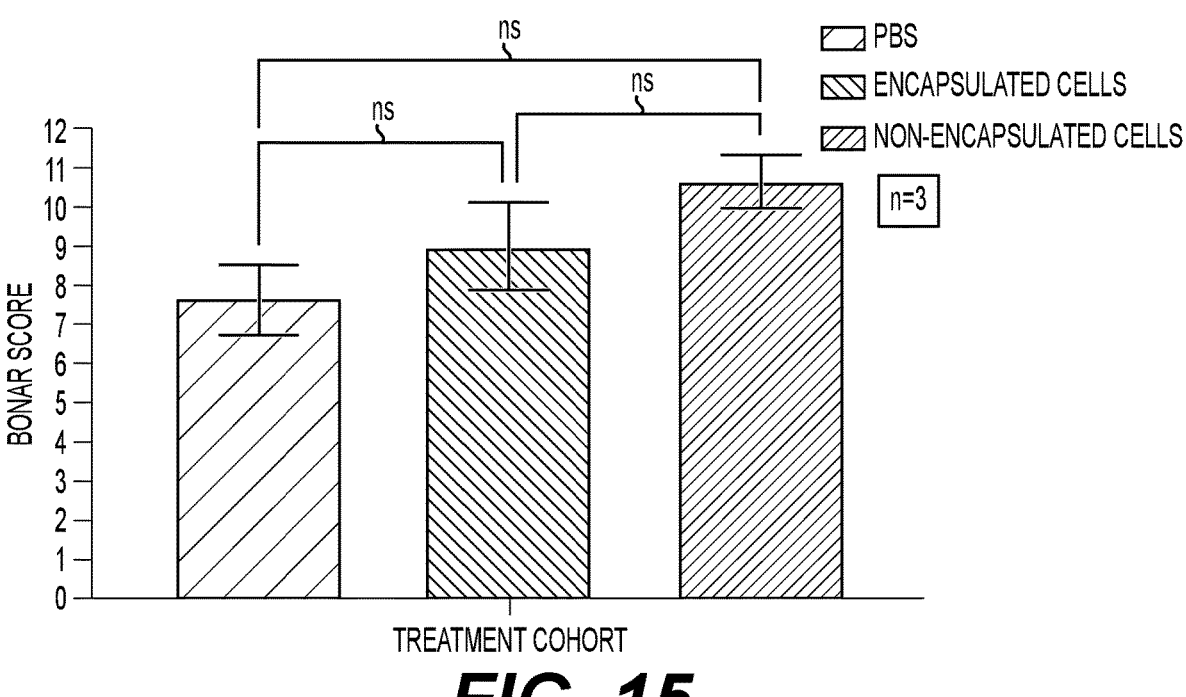
Figure 16:
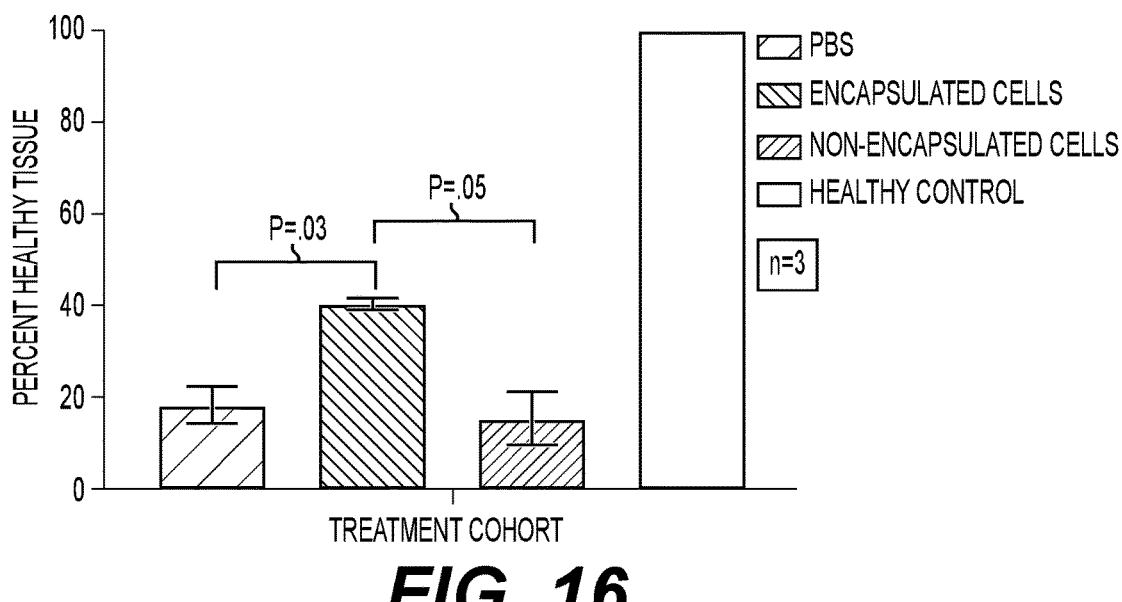
Figure 17:
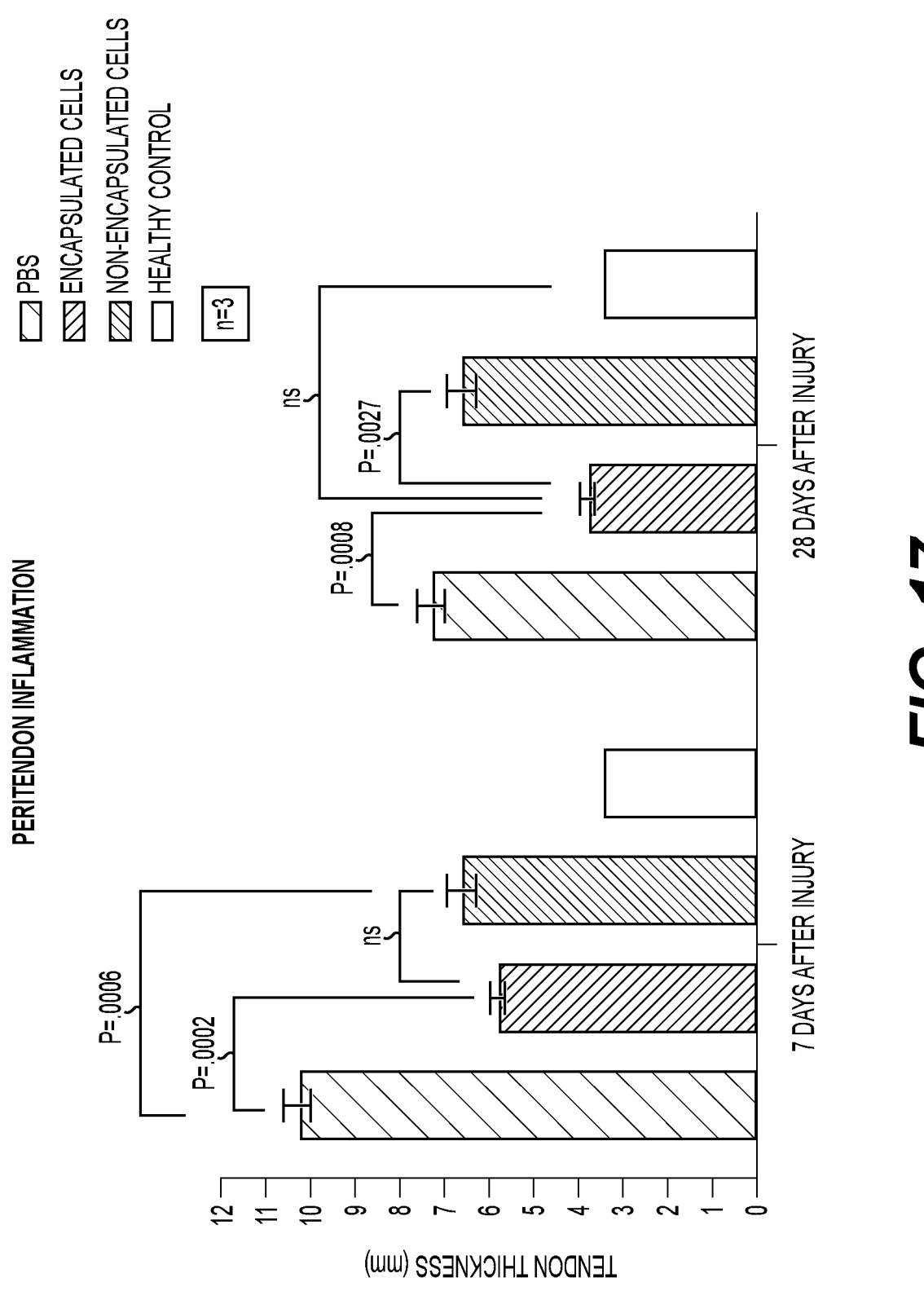
Figure 18:
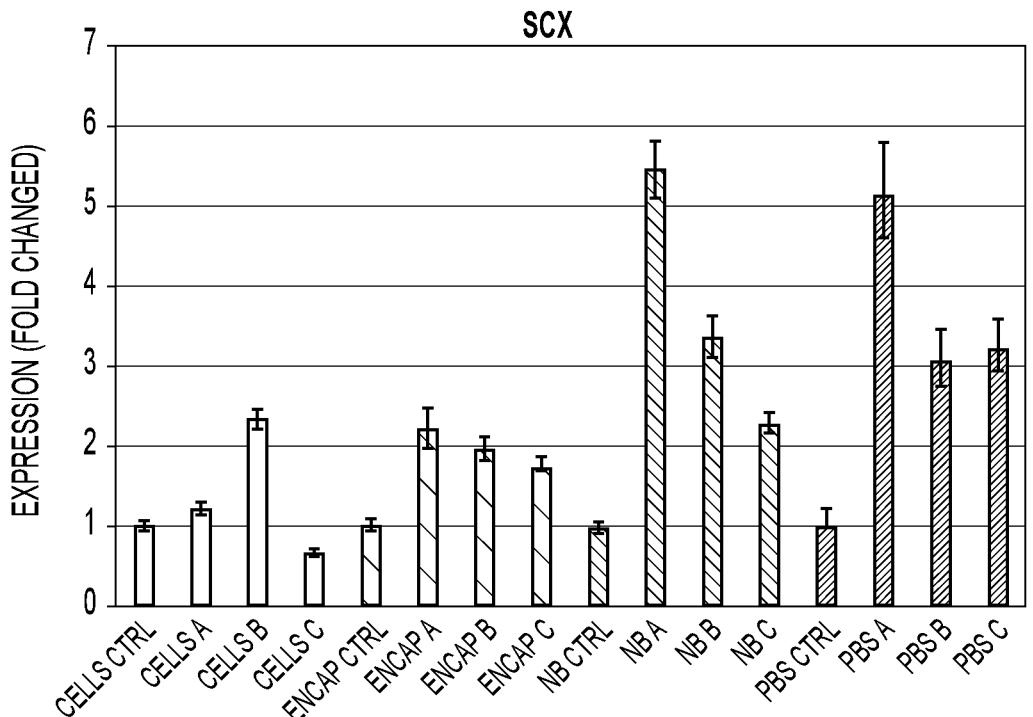
Figure 19:
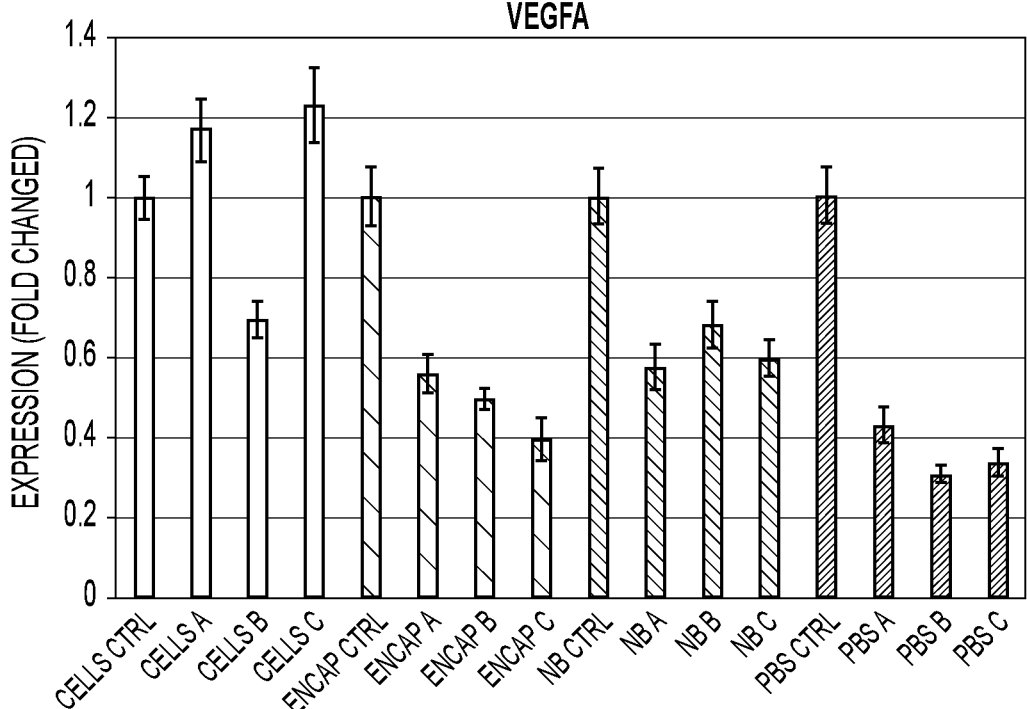

FIG. 9A shows relative expression of genes detected in encapsulated MSCs at day 0, day 7, and day 14;

FIG. 9B shows expression of genes detected in encapsulated MSCs normalized to the reference gene Hprt at day 0, day 7, and day 14;

FIG. 10 shows relative expression of the gene Gdf7 in encapsulated MSCs over time;

FIG. 11A shows fluorescent beads encapsulated in hydrogel droplets sticking to the surface of an Achilles tendon 24 hours after injection;

FIG. 11B shows fluorescent beads encapsulated in hydrogel droplets inside a punch wound 5 days after injection;

FIG. 11C shows a lack of retention of fluorescent beads that were not encapsulated in hydrogel droplets 5 days after injection;

FIG. 12 shows a lack of an increase in M1 macrophages by encapsulated cells;

FIG. 13A shows an H&E-EMS stained section of a healthy Achilles tendon;

FIG. 13B shows an H&E-EMS stained section of a encapsulated MSC-treated Achilles tendon;

FIG. 13C shows an H&E-EMS stained section of a non-encapsulated MSC-treated Achilles tendon;

FIG. 13D shows an H&E-EMS stained section of a PBS-treated Achilles tendon;

FIG. 14A is an illustration of rat Achilles tendon morphology;

FIG. 14B shows an H&E-EMS stained section of a healthy Achilles tendon;

FIG. 14C shows an H&E-EMS stained section of an encapsulated MSC-treated injured Achilles tendon;

FIG. 14D shows an H&E-EMS stained section of an untreated (PBS-control) injured Achilles tendon;

FIG. 15 shows Bonar scoring for an area of greatest pathology;

FIG. 16 shows percent healthy tissue in Achilles tendon 28 days after treatment;

FIG. 17 shows peritendon inflammation results 7 days and 28 days after injury;

FIG. 18 shows expression of scleraxis (SCX);

FIG. 19 shows expression of VEGF-A;

FIG. 20A shows a spleen pathology image; and

FIG. 20B shows a kidney pathology image.

The drawing figures do not limit the invention to the specific embodiments disclosed and described herein. The drawings are not necessarily to scale, emphasis instead being placed upon clearly illustrating the principles of the invention.

DETAILED DESCRIPTION

The subject matter of the invention is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claimed invention. Terms should not be interpreted as implying any particular ordering of various steps described unless the order of individual steps is explicitly described.

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of the equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Fabrication of hydrogel particles is widely applicable to a variety of industries and applications, including drug delivery and tissue regeneration. Fabrication of such hydrogel particles is typically achieved via dual phase systems, such as oil-water. Particles are formed by methods such as emulsification or microfluidic generation, resulting in an aqueous hydrogel particle suspended in a hydrophobic suspension media phase. Particles must subsequently be separated from the suspension media phase before use, as typical applications require a relatively suspension media-free environment for proper functioning of the cargo encapsulated therein. The suspension media removal process presents a number of challenges. For example, in applications such as live cell encapsulation, fast and gentle removal of the suspension media, or other substances, is paramount to endpoint viability. Similarly, in other examples, fast and gentle removal of the suspension media is required to maintain integrity and downstream efficacy of therapeutic particles such as drugs, RNA, DNA, proteins, viral packages, lipid encapsulated therapies, etc. In these cases, the in vivo potency of encapsulated material is paramount to desired therapeutic outcomes but is compromised due to current processing methods. As such, a significant problem in particle or cell encapsulation processes and methods is maintaining cell viability and/or cargo integrity during the suspension media removal process, without compromising the efficacy of said removal process and resulting end product purity.

Typically, removal of the suspension media from such mixtures requires extensive washing with high velocity centrifugation or aggressive detergents to completely remove the suspension media. These processes can be both time consuming and deleterious to any encapsulated cargo. For example, high velocity centrifugation to remove the suspension media dries out the cargo, adversely affecting the function, integrity, and/or viability of the cargo contained within the encapsulation matrix.

Embodiments of the invention solve the above-mentioned problems by providing a method for removing suspension media from hydrogel encapsulated cargo. This process uses a density adjusting media to create a protective barrier phase between the suspension media and the hydrogel encapsulated cargo during and after centrifugation. This process improves speed and efficiency of separation through dispersal of suspension media-aggregated particles and enables the hydrogel particles to be centrifuged at sufficient speeds and durations to completely remove the suspension media from the hydrogel-suspension media mixture for improved end product purity without drying out, damaging, or otherwise impacting the encapsulated cargo. The cargo viability, process speed and efficiency, and end product purity afforded by this process enables production of hydrogel encapsulated cargo (e.g., therapeutic cells) at sufficient quantities, purity, and therapeutic activities for high in vivo potency. Therapies relying on in vivo potency of encapsulated cargo such as living cell encapsulation for treatment of injuries and diseases are particularly benefited. A specific example of this is the encapsulation of mesenchymal stem cells for treatment of joint, tendon, and ligament pathologies; where previous methods could not elicit desired therapeutic outcomes in a commercially relevant manner due to insufficient encapsulated cell viability, undesirable cell behavior, and/or insufficient end product purity at needed production scales.

Context and Concepts of the Invention

In general, the terms and phrases used herein have their art-recognized meaning, which can be found by reference to standard texts, journal references, and contexts known to those skilled in the art. The following definitions are provided to clarify their specific use in the context of the invention.

As used herein, the term "cargo" refers to any article to be encapsulated within a scaffold. In embodiments of the present disclosure, this scaffold may be a hydrogel or hydrogel particles, as described in greater detail below. As non-limiting examples, cargo may refer to drugs, cells, exosomes, tissues, RNA, DNA, protein, viral vectors, lipid encapsulates, cell signaling factors, cellular scaffolding, caged nanoparticles, or others. In some embodiments, the cargo may be used for downstream therapeutic purposes. For example, cells such as mesenchymal stem cells, chondrocytes, osteoblasts, pancreatic islet cells, beta cells, neural cells, fibroblasts, vascular smooth muscle cells, pluripotent stem cells, or endothelial cells may be encapsulated in the scaffold (e.g., hydrogel particles). Collections of cells and cell products such as spheroids, organoids, and tissues may also be encapsulated. Any of the aforementioned examples may be applied to a patient for therapeutic purposes. As will be discussed in greater detail below, the viability and/or integrity of the cargo following the encapsulation process is essential for downstream uses.

As used herein, the term "polymer" refers to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments, greater or equal to 30 repeating units) and a high molecular weight (e.g., greater than or equal to 1 kDa, in some embodiments greater than or equal to 10 kDa, in some embodiments greater than or equal to 20 kDa, in some embodiments greater than or equal to 50 kDa or in some embodiments greater than or equal to 100-kDa). Polymers are commonly the polymerization product of one or more monomer or macromer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may comprise amorphous, semi-amorphous, crystalline, or semi-crystalline states.

As used herein, the term "monomer" and/or "macromer" refer to a reagent which can undergo polymerization under appropriate conditions. A monomer or macromer reagent comprises at least one monomer or macromer molecule, where a monomer or macromer molecule is a molecule which can undergo polymerization, thereby contributing constitutional units to the structure of a polymer or oligomer.

In embodiments, a monomer or macromer reagent may be represented by an average or dominant chemical structure and comprise monomer molecules having that chemical structure, but may also contain components with other chemical structures. For example, a monomer or macromer reagent may comprise impurities having chemical structures other than the average or dominant structure of the reagent. Macromer may refer to a reagent which is polymeric, e.g., has a number of repeating units but may further undergo polymerization to form a polymer of macromer repeating units. In some embodiments, macromer refers to reagents having a high molecular weight (e.g., greater than or equal to 200 Da, in some embodiments greater than or equal to 1000 Da, or in some embodiments greater than or equal to 10,000 Da).

As used herein, the term "hydrogel" refers to an at least partially hydrophilic substance being characterized by high water absorbency. In embodiments, hydrogel comprises an at least partially hydrophilic polymer, superabsorbent polymer, or biomacromolecule, for example in a network configuration. Hydrogels may be characterized as a water swollen but insoluble or partially insoluble substance. In some embodiments, hydrogels may absorb water greater than or equal to 10 times the hydrogel weight, greater than or equal to 50 times the hydrogel weight, or, optionally, greater than or equal to 100 times the hydrogel weight.

As used herein, the term "microparticles" or "hydrogel particles" refers to particles including polymers, having relatively small dimensions including diameter, radius, height, width, depth, etc. In some embodiments, for example, microparticles or hydrogel particles refer to particles having a lateral dimension (e.g., diameter) of less than or equal to 1 mm. In some embodiments, microparticles or hydrogel particles refer to particles having an average or mean diameter of less than or equal to 500 μm, less than or equal to 100 μm, or less than or equal to 50 μm. In some embodiments, microparticles refer to particles having lateral dimensions selected from the range of 10 nm to 1000 μm. In some embodiments, microparticles are microspheres. References to "microparticles" or "hydrogel particles" disclosed herein may refer to microparticles or hydrogel particles, respectively, that include or exclude encapsulated cargo. Said another way, reference to "microparticles" or "hydrogel particles" may or may not include encapsulated cargo, and need not explicitly state so.

As used herein, the term "click chemistry" refers to biocompatible small molecule reactions used in bioconjugation that allows the joining of substrates with specific biomolecules. For example, click chemistry may refer to chemical reactions that quickly and irreversibly react, forming a high yield of a single reaction product with high reaction specificity. Click chemistry reactions, as used herein, may be particularly beneficial for the formation of hydrogel particles.

As used herein, the term "density adjusting media" refers to a media having a density within a predetermined range. For example, the density of the density adjusting media may be between the density of suspension media and the density of the hydrogel solution. As will be discussed in greater detail below, in some embodiments the density adjusting media may be a liquid having a density of between about 1.0 g/mL to about 2.0 g/mL. In some embodiments, the density adjusting media may be a liquid having a density of between about 1.1 g/mL to about 1.5 g/mL. In some embodiments, the density adjusting media may be a liquid having a density of about 1.3 g/mL. In some embodiments, the density adjusting media is cytocompatible. As further described below, the density adjusting media may be used to assist with physically separating suspension media from hydrogel.

Polyethylene glycol (PEG)-based polymers are regarded for their robust mechanical properties, elasticity, and biocompatibility. PEG polymers are easily modified with reactive groups, an example being PEG norbornenes (PEGNB), which uses dithiolated PEG as a linear crosslinker to facilitate the stepwise linking of thiol and ene (Thiol-Ene) units via a radical mediated reaction. Compared to other synthetic monomers, PEG hydrogels using Thiol-Ene mediated crosslinking reactions are beneficial due to their biocompatibility and chemical versatility, proceeding via simple "click" chemistry, and allowing modification with a range of monofunctional or multifunctional moieties. Such click chemistry reactions are widely used in industrial applications including pharmaceutical synthesis, material coatings, and nanotechnology. Based on these characteristics, a class of photopolymerizable PEG-based hydrogels has been developed around click chemical reactions.

Photopolymerization is a convenient and cytocompatible alternative to solvent-based or thermal curing, and can be carried out both in-vitro and in-vivo. The photoinitiated free radical polymerization of PEGs or other suitable monomer or macromer modified with click reactive functional groups is typically performed in the presence of a photoactive initiator that generates free radicals upon exposure to ultraviolet light. Whereas some free radical polymerization is strongly inhibited by oxygen (e.g., Acrylate reactions), click reactions, such as between thiol and vinyl groups, are not strongly oxygen inhibited, and actively consume reactive oxygen species. This is advantageous when engineering microscale structures where the inhibition of photopolymerization reactions is exacerbated due to increased surface-to-volume ratios.

PEGNB is attractive to use as a cell encapsulant and tissue scaffold because of its tissue-like physical properties, which can be tailored to closely mimic extracellular matrices, cytocompatibility, and synthetic versatility. Over a certain polymer composition range, highly water-swollen PEGNB hydrogel networks have been proven to be cytocompatible encapsulants for many cell types. Synthetic customization of PEGNB macromolecular architecture and chemistry provides a large diversity of properties, making it an attractive alternative to natural hydrogels. PEGNB hydrogel networks can be decorated with cell-adhesive peptide groups (e.g., cysteine-arginine-glycine-asparagine-serine (CRGDS)) that allow the formation of bioactive hydrogels that promote cell adhesion, spreading, and tissue elaboration. Modifications to the PEG crosslinker can provide an ability to spatially and temporally remodel the hydrogel by hydrolytic, proteolytic, or optical degradation. Directed network remodeling has become widely used as a strategy for temporally regulating hydrogel properties.

Microscale hydrogel particles, or "microgels" are of emerging importance to the sensing, drug, and tissue engineering communities due to intraparticle diffusion, facile antibody or oligonucleotide conjugation, and potential for in vivo applications. PEG microgels have typically been fabricated via stop-flow lithography, a single-phase microfluidic stepwise photopolymerization technique, or via microfluidic emulsion, involving forming droplets in a continuous suspension media phase at intersecting microfluidic channels or coaxial capillaries. However, microfluidic processes to produce these PEG microgels may not be sufficient to achieve therapeutically relevant cargo-to-droplet ratios. For example, when the cargo to be encapsulated are cells having a radius of between about 100 μm to about 500 μm, a therapeutically relevant ratio may be any ratio above 3 cells per particle. Such ratios are difficult to achieve via microfluidic production due to cell clumping within the microfluidic device. At such high titers, cells are more likely to interact and stick together due to proteins expressed at the cellular membrane, released signaling molecules and peptides, or other reasons. This causes certain droplets to contain too many cells, so that cellular apoptosis is triggered, and many droplets to contain no cells. Alternatively, PEG microspheres may be fabricated at higher rates than stop-flow lithography by emulsifying two-phase oil-water suspensions. Furthermore, microsphere fabrication via emulsification, as described, foregoes the requirement of complex, expensive instruments, thereby reducing costs associated with production and potential breakdown/maintenance of the complex instruments. Microparticles may be prepared by bulk aqueous phase emulsification via sonication, vortexing, or homogenization. Following emulsification, stabilized particles suspended within the suspension media (e.g., immiscible oil) are photopolymerized by near ultraviolet (UV) irradiation. For downstream applications and efficacy of the cargo, the suspension media must then be thoroughly removed from the hydrogel. The suspension media removal step of prior technologies has prevented scaling and widespread use of the bulk two-phase oil-water suspensions. For example, one prior technique uses high-speed centrifugation of the product to "pull-down" the suspension media from the mixture. This immediately dehydrates the encapsulated cargo, thereby negatively impacting the integrity/efficacy of the encapsulated cargo. Prior techniques have attempted to work around this problem in a number of ways. For example, some prior techniques attempt to remove suspension media from the hydrogel-suspension media mixture by using many (e.g., seven or more) washing steps, which typically involve pipetting the mixture up and down in between low-speed centrifugation steps (e.g., about 150 relative centrifugal force (rcf)), at which speed is not sufficient to remove all of suspension media. This process has many downsides, including: a) significantly increasing the time necessary for the separation process, effects of which include deleteriously impacting encapsulated cargo (e.g. cell viability), production throughput, and production expense; b) decreasing the overall yield of viable cargo encapsulated particles due to particles sticking together—a result of hydrophobic interaction between suspension media covered particles, c) sticking of the particles to certain components used during the multiple washing steps; d) low throughput process since all the particles must be delicately hand washed; e) high levels of impurities in the end product due to low centrifugation speeds (e.g., less than about 150 rcf) or insufficient centrifugal times (e.g., less than 1 minute) required to not dehydrate and/or damage the cargo; and f) failure to fully remove suspension media from the hydrogel also due to low centrifugation speeds (e.g., full removal of suspension media from the particles requires centrifugation speeds of about 700 rcf or greater or of lower centrifugation speeds, e.g., less that 700 rcf, for at least one minute). These downsides, both in whole and in part, prevent current methods from producing encapsulated cargo in sufficient quantity, of sufficient quality, and of sufficient purity for many target uses (e.g. production via Current Good Manufacturing Practices (CGMP) and regulatory approval for in vivo administration in a commercial capacity). Other methods attempt to circumvent these issues using aggressive detergents that deleteriously impact cargo viability and function, or methods like core-shell spherification that require acidic conditions during processing, eliciting similar undesirable effects on cargo.

Hydrogel Particle Production and Purification

Figure 1:
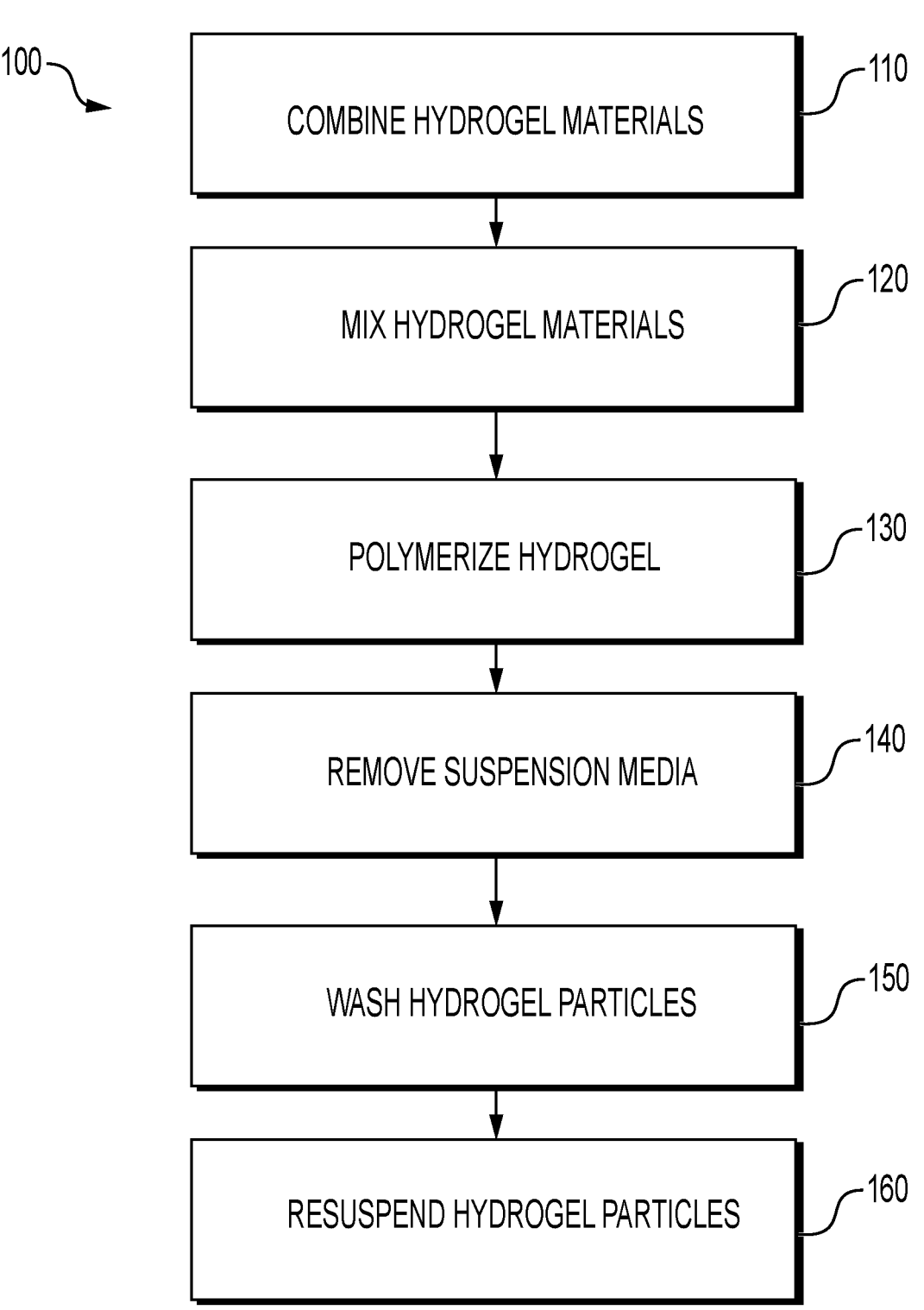
FIG. 1 depicts some embodiments of a hydrogel particle encapsulation and suspension media removal method for generating and purifying hydrogel particles having encapsulated cargo.

With reference now to FIG. 1, an exemplary hydrogel particle encapsulation and suspension media removal method 100 for generating and purifying hydrogel particles is shown. Descriptions of some steps of method 100 will be discussed in greater detail below with reference to the corresponding figures.

In a step 110, hydrogel materials are combined. In an example of step 110, a hydrogel polymer, a linker, a cargo suspension, a suspension media, and a surfactant are combined to generate the hydrogel mixture. As will be discussed below, in some embodiments a photoinitiator may be added to aid in photopolymerization. In some embodiments, one or more of the aforementioned components may be mixed with one another prior to generating the final hydrogel mixture. For example, the hydrogel polymer (e.g., 10% by weight), the linker (e.g., 10 millimol linker), the photoinitiator (e.g., 0.1% by weight), and the cargo suspension may be mixed together to form a first mixture, and separately the suspension media and the surfactant may be mixed to form a second mixture (e.g., at about 2% surfactant). The first mixture and the second mixture may then be combined to generate the hydrogel mixture.

In some embodiments, the ratio of the first mixture to the second mixture may be 1:1 to about 1:10. In some embodiments, the ratio of the first mixture to the second mixture may be between about 1:1 to about 1:5. In some embodiments, the ratio of the first mixture to the second mixture may be about 1:3.

In some embodiments, the second mixture may comprise a suspension media having between about 0.001% to about 1% surfactant. In some embodiments, the second mixture may comprise a suspension media having between about 1% to about 5% surfactant. In some embodiments, the surfactant may be anionic, cationic, or zwitterionic. In some embodiments, the surfactant may be a non-ionic surfactant (e.g., ethoxylates, fatty alcohol ethoxylates, alkylphenol ethoxylates, fatty acid ethoxylates, ethoxylated amines, fatty acid amides, fatty acid esters of polyhydroxy compounds, fatty acid esters of glycerol, fatty acid esters of sorbitol, fatty acid esters of sucrose, alkyl polyglucosides, etc.).

The suspension media used is configured to not damage the cargo. In embodiments, the suspension media is hydrophobic to serve as a hydrophobic suspension media for hydrophilic material such as hydrogel material. In some embodiments, the suspension media used may allow for oxygen delivery/consumption by the cargo (e.g., in the case that the cargo comprises viable cells). In some embodiments, the suspension media may be an oil such as NOVEC™ 7500 oil (3M™), halocarbon oil, mineral oil, or similar; further, a fluorinated version of these oils, or other engineered hydrophobic fluid suitable for creating two phase suspensions may be used. For example, a fluorosurfactant such as RAN 008-FluoroSurfactant (RAN Biotechnologies, Beverly, MA) may be mixed with the oil to provide a final concentration of 0.02% to 2% fluorosurfactant. In certain embodiments, the RAN 008-FluoroSurfactant is mixed with NOVEC™ 7500 oil with a final concentration of 2%.

In some embodiments, the hydrogel polymer may be any one or combination of hyaluronic acid, cartilage, gelatin, chitosan, heparin, alginate, fibrin, polyvinyl alcohol, PEG, sodium polyacrylate, or similar. In some embodiments, the hydrogel polymer may be functionalized with reactive groups such as acrylate, methacrylate, thiol, tetrazine, azide, aminooxy, etc. In some embodiments, the hydrogel polymer may be any one or combination of PEG-based polymers, such as PEG, PEG diacrylate (PEGDA), PEG Norbornene (PEGNB), PEG maleimide, PEG cyclooctyne, PEG triarylphosphine or PEG disulfide. In some embodiments, the hydrogel polymer may be of a specific weight. For example, the hydrogel polymer may be between about 250 Da to about 20 kDa. In some embodiments, the hydrogel polymer may be between about 20 kDa to about 250 kDa. In some embodiments, PEG groups may possess various geometries including Branched PEGs, Star PEGs or Comb PEGs.

In some embodiments, the linker may be any one or combination of thiol, acetylene, vinyl Sulphone, azide, amine, acid, methyl Ether, Diol, tetrazine, aminooxy, etc.

In some embodiments, the photoinitiator may be any compound that catalyzes the crosslinking and polymerization of the hydrogel. For example, the photoinitiator may be any one or combination of lithium phenyl-2,4,6-trimethyl-benzoylphosphiante (LAP), or vitamin B2 combined with triethanolamine (B2/TEOA), 2-dimethoy-2-phenylaceto-phenone (DMPA), 2-hydroxy-4-(2-hydroxyethoxy)-2-meth-ylpropiophenone (I2959). In some embodiments, LAP may be advantageous for this process. LAP enables efficient photopolymerization around near visible spectra of UV light, thereby avoiding DNA damage associated with UV and far UV spectrum.

As mentioned above, the cargo suspension may have cargo including any one or combination of the following: drugs, cells, viable cells (e.g., mammalian cells), RNA, DNA, protein, viral vectors, lipid encapsulates, cell signaling factors (e.g., exosomes), cellular scaffolding, caged nanoparticles, or others.

Figure 3:
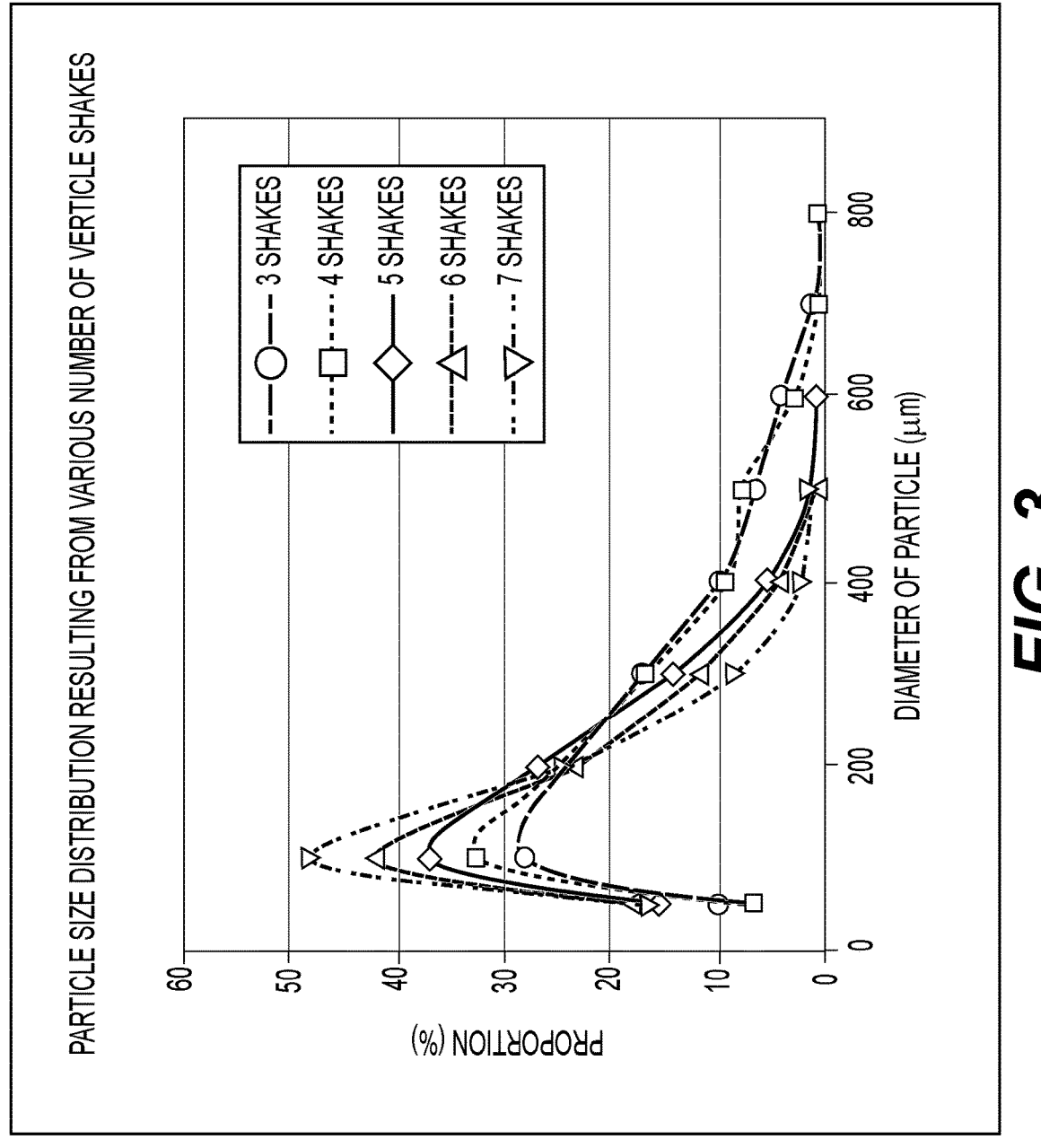
FIG. 3 is a graph showing the effects of the number of vertical shakes on the size distribution of hydrogel particles, in some embodiments.

In a step 120, the hydrogel mixture is mixed. In an example of step 120, mixing the hydrogel materials comprises: 1) accelerating a container holding combined hydrogel materials in a first direction, 2) decelerating the container to a stop, 3) accelerating the container in a second (opposite) direction back to an initial position, and 4) repeating steps 1-3 a plurality of times. For example, the hydrogel materials may be mixed via shaking a tube containing the hydrogel mixture by hand, or via a shaking device, in a vertical up and down motion. An exemplary shaking device is a Liquid Shaker gel varnish/polish shaking machine (foreverLily), which has a shaking motion distance of about ¾-inch and is used with tubes from 1.5 to 5 mL. Larger tubes (e.g., 100 mL) may be used with shaking by hand or a larger shaking device. A speed of the shaking device may be adjustable (e.g., from one shake per second to six shakes per second). In certain embodiments, the speed is set to four shakes per second and the shaking duration is approximately one second. Importantly, the number of vertical shaking steps can be used to effect the size of the resulting hydrogel particles. For example, as illustrated in FIG. 3, following three vertical shakes roughly 28% of the hydrogel particles are about 100 μm and roughly 10% of the hydrogel particles are about 400 μm. In another example, following five vertical shakes roughly 37% of the hydrogel particles are about 100 μm and roughly 5% of the hydrogel particles are about 400 μm. In another example, following 7 vertical shakes roughly 48% of the hydrogel particles are about 100 μm and roughly 2% of the hydrogel particles are about 400 μm.

Also importantly, as mentioned above, mechanical agitation (e.g., vortexing, sonicating, and/or homogenizing) of the hydrogel materials in a non-vertical shaking manner, may lead to polydispersity, decreasing the size of a portion of the hydrogel particles such that 3 or fewer cells/cargo are able to be combined. Accordingly, in some embodiments the shaking of the hydrogel materials is performed with between about 0.5 Newtons to about 5000 Newtons of force, determined using an accelerometer, to form hydrogel particles that are between about 80 μm to about 500 μm.

In a step 130, the hydrogel is polymerized. In an example of step 130, the hydrogel mixture is photopolymerized using a light source. For example, the hydrogel mixture may be exposed to UV light or near UV light at a specific wavelength, a specific energy, and a specific time to cause polymerization of the hydrogel polymers contained within. In some embodiments, the wavelength of the UV light may be between about 365 nm to about 435 nm. In some embodiments, the energy of the UV light may be between about 1 mW/cm$^2$ to about 200 mW/cm$^2$. In some embodiments, the energy of the UV light may be between about 50 mW/cm$^2$ to about 150 mW/cm$^2$. In some embodiments, the energy of the UV light may be about 100 mW/cm$^2$. In some embodiments, the hydrogel mixture may be exposed to UV light for a period of between about 0.1 seconds to about 40 seconds. In some embodiments, the hydrogel mixture may be exposed to UV light for a period of between about 1 second to about 30 seconds. In some embodiments, the hydrogel mixture may be exposed to UV light for a period of about 20 seconds.

Importantly, the wavelength, intensity, and duration of the UV light exposure heavily affects the polymerization of the hydrogel material. For example, if the hydrogel mixture is exposed for too long a duration or at too high of an intensity, then the hydrogel material may become too heavily polymerized and prevent downstream resuspension of the hydrogel particles. Alternatively, if the hydrogel material is exposed for too short a duration or at too low of an intensity, then the hydrogel material will not be sufficiently polymerized to properly encapsulate the cargo within.

In some embodiments, methods other than photopolymerization may be used to induce polymerization of the hydrogel. For example, temperature, radiation, electricity, chemical, enzymatic, or other means for inducing polymerization may each be alternatively used at step 130 to cause polymerization of the hydrogel. In some embodiments, wavelengths other than the UV spectrum may be used for photopolymerization. In some embodiments infrared (IR) light may be used. For example, wavelengths of between about 700 nm to about 1 mm may be used for photopolymerization.

Figure 2:
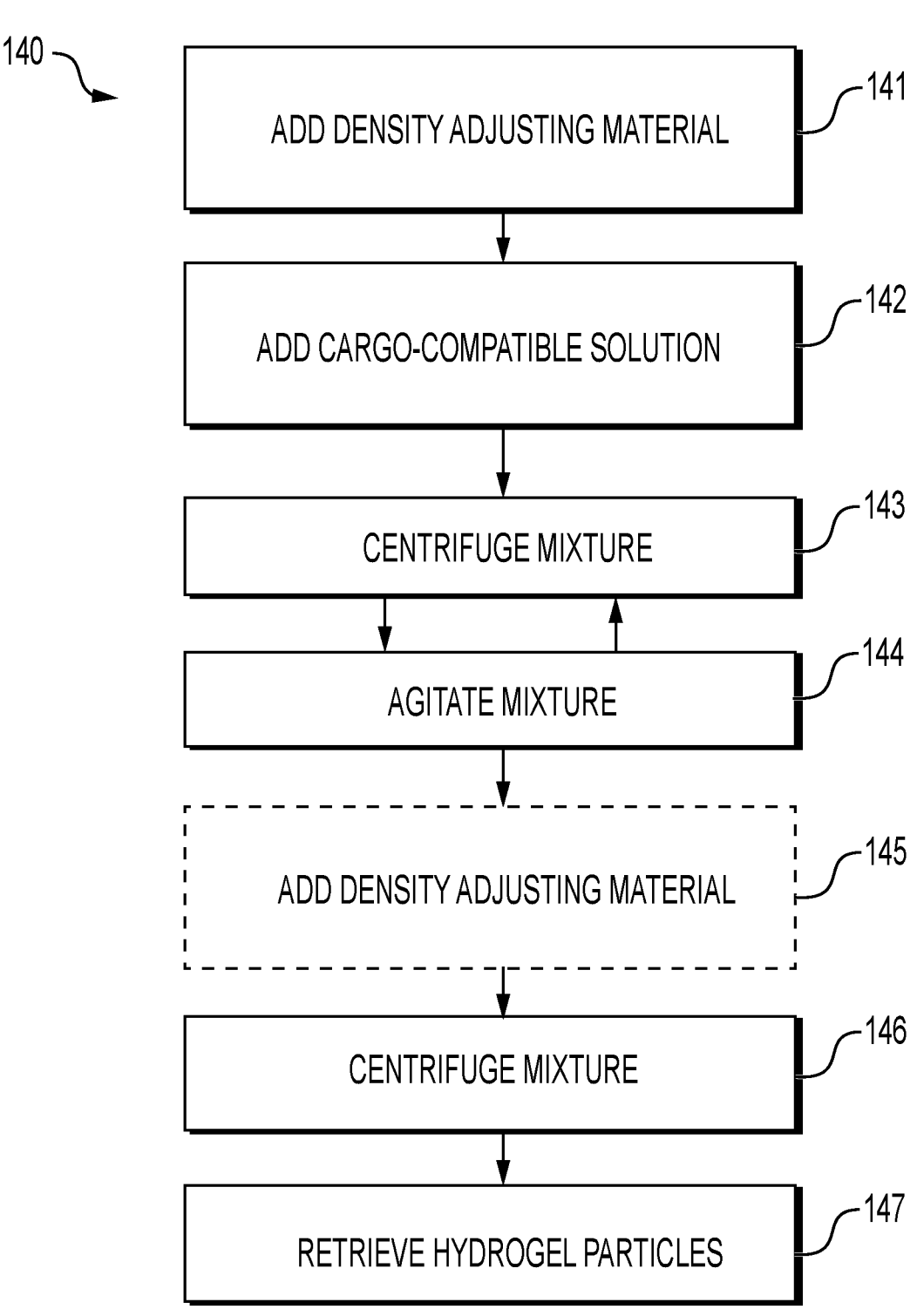
FIG. 2 depicts some embodiments of a method for removing suspension media from a hydrogel-suspension media mixture.

In a step 140, suspension media is removed from the hydrogel mixture for purifying the hydrogel particles from the suspension media. With reference to FIG. 2, step 140 is shown in some embodiments as a process having multiple sub-steps.

In a step 141, a density adjusting material is added to the hydrogel-suspension media mixture. The density adjusting material may be an aqueous solution configured to separate the hydrogel solution from the suspension media (e.g., by forming a three-phase layered solution having the density adjusting material located in the middle phase). In an example of step 141, a density adjusting material is added to the hydrogel-suspension media mixture at a ratio of 1:2 (1 part density adjusting material to 2 parts hydrogel-suspension media mixture). In some embodiments, the density adjusting material is added to the hydrogel-suspension media mixture at a ratio between about 1:0.5 to about 1:5.

The density adjusting material is configured to be a certain density to allow for separation of the suspension media from the hydrogel solution based on density differences therebetween. For example, in some embodiments the density adjusting material is between about 1.1 g/mL to about 1.6 g/mL. In some embodiments, the density adjusting material is between about 1.2 g/mL to about 1.4 g/mL. In some embodiments, the density adjusting material is about 1.3 g/mL. In some embodiments, the density of the density adjusting material may be adjusted according to the density of the suspension media used. For example, if a suspension media is used at a density of 2.5 g/mL, then the density adjusting material may have a density greater than the density of the microparticle density but less than the density of the suspension media, which in this example would be less than 2.5 g/mL.

In some embodiments, different solutions having the above densities may be used as the density adjusting material. For example, the density adjusting material may be any one or combination of optiprep or iodixanol. It is further contemplated that the density adjusting material is compatible with the encapsulated cargo, and certain solutions may be chosen based on the encapsulated cargo. It is contemplated the density adjusting material may have one or a number of surfactants added, suitable for furthering the removal of suspension media from particles.

In a step 142, a cargo-compatible solution is added. In an example of step 142, a cargo-compatible solution containing a cargo-compatible surfactant is added to the mixture. In some embodiments, the cargo-compatible solution is added at a ratio between about 1:0.5 to about 1:4 (1 part cargo-compatible solution to 4 parts hydrogel mixture+density adjusting material). The cargo-compatible surfactant may aid in the separation of the suspension media from the hydrogel material. In some embodiments, the cargo-compatible surfactant may be anionic, cationic, or zwitterionic. In some embodiments, the cargo-compatible surfactant may be a non-ionic surfactant (e.g., ethoxylates, fatty alcohol ethoxylates, alkylphenol ethoxylates, fatty acid ethoxylates, ethoxylated amines, fatty acid amides, fatty acid esters of polyhydroxy compounds, fatty acid esters of glycerol, fatty acid esters of sorbitol, fatty acid esters of sucrose, alkyl polyglucosides, etc.). In some embodiments, the cargo-compatible solution includes any one or combination of Dulbecco's Modified Eagle Medium (DMEM), Fetal Bovine Serum (FBS), Penicillin, Streptomycin, phosphate-buffered saline (PBS), Normal Saline, Lactated Ringers, or any other biocompatible or drug relevant solution.

In a step 143, a three-phase solution is formed. In an example of step 143, the mixture is centrifuged to form a three-phase solution as described below. In some embodiments, the mixture may be centrifuged for a period of between about 30 seconds to about 10 minutes. In some embodiments, the mixture may be centrifuged for a period of between about 30 seconds to about 5 minutes. In some embodiments, the mixture may be centrifuged at a force of between about 200 rcf to about 900 rcf. In certain embodiments, the mixture may be centrifuged for 3 minutes at a force of 350 rcf.

The three-phase solution has an upper phase being the aqueous phase containing hydrogel, a middle phase being the density adjusting material phase, and a bottom phase being the suspension media phase. Such a three-phase distribution provides a physical barrier (i.e., the middle phase) between suspension media (i.e., lower phase) and the aqueous (i.e., upper phase) which assists with facile separation of the suspension media from the hydrogel. During experimental procedures, formation of the three-phase solution was unexpected because the hydrogel material was anticipated to partially or fully form a miscible mixture with the density adjusting material during centrifugation due to both being hydrophilic. For example, some embodiments of the density adjusting material (e.g., optiprep) were expected to form a miscible mixture with the hydrogel material due to both being hydrophilic despite their differences in density. Accordingly, a three-phase solution following the addition of the density adjusting material was unexpected. During and following the forced separation achieved by centrifugation, the three-phase solution persists for minutes to hours, which is used to separate the suspension media from the hydrogel material. Such a separation of phases, with the middle phase settling between the suspension media and the aqueous hydrogel containing phase, improves purification of the hydrogel particles from the suspension media, while preventing the cargo (e.g., cells) from drying out, which is critical for maintaining viability of the cargo and thereby its biologic activity. Distribution of the hydrogel at the bottom of the upper aqueous phase prevents the cargo from being exposed to air.

In a step 144, the mixture is mechanically agitated. In an example of step 144, the mixture is mechanically agitated with a mechanical mixing device (e.g., a Scientific Industries GENIE G560 Vortex-Genie 2) using a force of about 1 Newton per 300 μl of particles about 20 times to dislodge the hydrogel/suspension media clump. For example, hydrogel/suspension media clumps are portions of hydrogel particles that are partially held together due to trapped suspension media held therebetween. The trapped suspension media not only causes the hydrogel particles to stick to one another, but the clumps may also stick to the side of the container. To sufficiently remove the suspension media from the hydrogel particles, the hydrogel/suspension media clumps may need to be dislodged from the side of the container. Accordingly, a clear or substantially transparent container may be used to visually inspect for hydrogel/suspension media clumps. In some embodiments, a force of between about 0.5 Newtons to about 5000 Newtons is used to dislodge the hydrogel/suspension media clumps. In some embodiments, the mechanical agitation may be performed between about 3 times to about 40 times. Since step 144 is performed after the cargo has been encapsulated in the appropriately sized hydrogel particles in steps 130 and 140, mechanical agitation may be used at this step without affecting the size of the particles and the amount of cargo encapsulated.

Following step 144, process 140 of method 100 may return to step 143 to repeat centrifugation of the mixture. It is contemplated that steps 143 and 144 may be repeatedly performed until the suspension media is substantially separated from the hydrogel. For example, steps 143 and 144 may be repeated until the hydrogel/suspension media clumps are substantially broken apart based on a visual inspection through a substantially transparent container. In some embodiments, steps 143 and 144 may be repeated between about 2 times to about 8 times. In some embodiments, steps 143 and 144 may be repeated about 4 times. Following repetition of steps 143 and 144, process 140 may proceed to optional step 145.

In an optional step 145, more density adjusting material is added to the mixture. In an example of optional step 145, additional density adjusting material is added to the mixture to obtain a ratio of about 1:5.5 to increase the size/amount of the middle density adjusting material phase. For example, due to the mechanical agitation in step 144 the middle density adjusting material phase may decrease in size/amount due to some portion of it being displaced into the upper phase. Accordingly, adding an additional layer may aid in a final step of centrifugation to pull out any additional suspension media that may be leftover in the hydrogel phase.

In some embodiments, the same amount of density adjusting material may be added in optional step 145 as added in step 141.

In a step 146, the mixture is centrifuged for a final time to separate the suspension media from the hydrogel material. In an example of step 146, the mixture is centrifuged at 350 rcf for 3 minutes. In some embodiments, the mixture at step 146 may be centrifuged at a force of between about 200 rcf to about 900 rcf. In some embodiments, the mixture at step 146 may be centrifuged for a period of between about 30 seconds to about 10 minutes.

In a step 147, the hydrogel particles are retrieved from the mixture. In an example of step 147, the hydrogel particles now void of suspension media, are retrieved from the upper phase. As discussed above, the hydrogel particles in the upper phase will be mostly sequestered from the density adjusting material middle phase. Accordingly, the upper phase may be easily retrieved (e.g., by pipetting) and transferred to a different container for further processing and/or downstream applications. Because the hydrogel particles are less dense than the middle phase, the hydrogel particles remain on top of the middle phase. Since the hydrogel particles should be protected from air, the cargo compatible aqueous phase of lesser or equal density is on top. Thus, the particles are sandwiched between the middle phase material and the upper phase solution. To remove the particles, one simply retrieves the upper phase (i.e., hydrogel particles and cargo compatible solution).

Referring now back to FIG. 1, in a step 150 the hydrogel particles are washed. In an example of step 150, following retrieval of the hydrogel particles in the upper phase, the hydrogel particles are placed on a filter and subsequently washed with the proper medium. In some embodiments, the hydrogel particles may be placed on a filter having a mesh properly sized to allow for any extra material leftover within the hydrogel mixture to flow through. For example, the mesh filter may have a mesh size of between about 5 μm to about 80 μm. However, it is contemplated that the size of the mesh filter may be chosen based on the size of the hydrogel particles generated in step 120. For example, the size of the mesh filter need be smaller than the hydrogel particles to retain them while other smaller material is allowed to flow through. It is further contemplated that in some embodiments, the mesh filter may be sized to allow for certain sized hydrogel particles to flow through thereby retaining only hydrogel particles of a certain size. For example, a 100 μm mesh filter may be used in step 150 such that any hydrogel particles having a size smaller than 100 μm may be washed through while any hydrogel particles having a size greater than 100 μm may be retained atop the mesh filter. Such capabilities allow for targeted retention of specific sized hydrogel particles that may have certain benefits in downstream applications.

Following placement of the hydrogel particles atop the mesh filter, the hydrogel particles are subsequently washed using a proper media. For example, the media may be chosen based on its compatibility with the cargo encapsulated within the hydrogel particles. Similarly, media may be chosen to not alter the integrity of the hydrogel particles. Example media used in this step may include DMEM, FBS, Penicillin, Streptomycin, PBS, Normal Saline, Lactated Ringers, or any other biocompatible or drug relevant solution. In some embodiments, the hydrogel particles may be washed with the media that the hydrogel particles will be stored in for subsequent applications. In some embodiments, the hydrogel media may be stepwise washed out of the media that was used in the centrifugation steps (e.g., in step 142) and into a media that will be used in subsequent applications (e.g., a storage solution). For example, some cargo may be sensitive to rapid changes in media. Accordingly, the media, or contents within the media, may be gradually changed in a stepwise manner to lower deleterious effects on the cargo. As an example of this, in step 142 the cargo-compatible solution may be PBS; however, following retrieval and washing of the hydrogel particles along with the encapsulated particles, it may be advantageous to have the hydrogel particles suspended in a different media (e.g., DMEM). To avoid a rapid change between the two media, multiple wash steps may be performed in which PBS is diluted at progressively higher ratios with DMEM until the final wash step lacks PBS. For instance, in five wash steps, the first wash may be PBS, the second wash may be 4 PBS:1 DMEM, the third wash may be 2 PBS:1 DMEM, the fourth wash may be 1 PBS:2 DMEM, and the fifth wash may be DMEM. This example is not to be construed as limiting as any combination and number of washes may be used depending on the encapsulated cargo and the optimum media for downstream applications.

It is contemplated that washing of the hydrogel particles may be performed using gravitation based (e.g., drip method), suction based (e.g., vacuum), or low-speed centrifugal based (e.g., at roughly 150 rcf for about 30 seconds) separation methods. These methods may be used to remove the washed liquid and corresponding debris from the mixture. In some embodiments, there may be one or more wash steps. For example, the hydrogel particles may be washed 1, 2, 3, 4, 5, or more times to sufficiently clear any leftover material from the particles.

In a step 160, the hydrogel particles are resuspended. In an example of step 160, the hydrogel particles are resuspended using a sufficient amount of solution and gentle agitation. For example, the hydrogel particles may be resuspended in a solution that is both cargo-compatible and suited for downstream applications (e.g., therapeutic use). In some embodiments, the hydrogel particles may be resuspended using pipetting, mechanical perturbance, or another gentle mechanical agitation method to resuspend them in the solution. In some embodiments, the hydrogel particles may be collected at the bottom of the container so as to store them for future use. For example, the hydrogel particles in the resuspension media may be centrifuged at a low speed and short period of time (e.g., about 300 rcf for about 5 minutes) to collect the hydrogel particles. Alternatively, the resuspended hydrogel particles may be immediately used for downstream purposes without collection.

Figure 4:
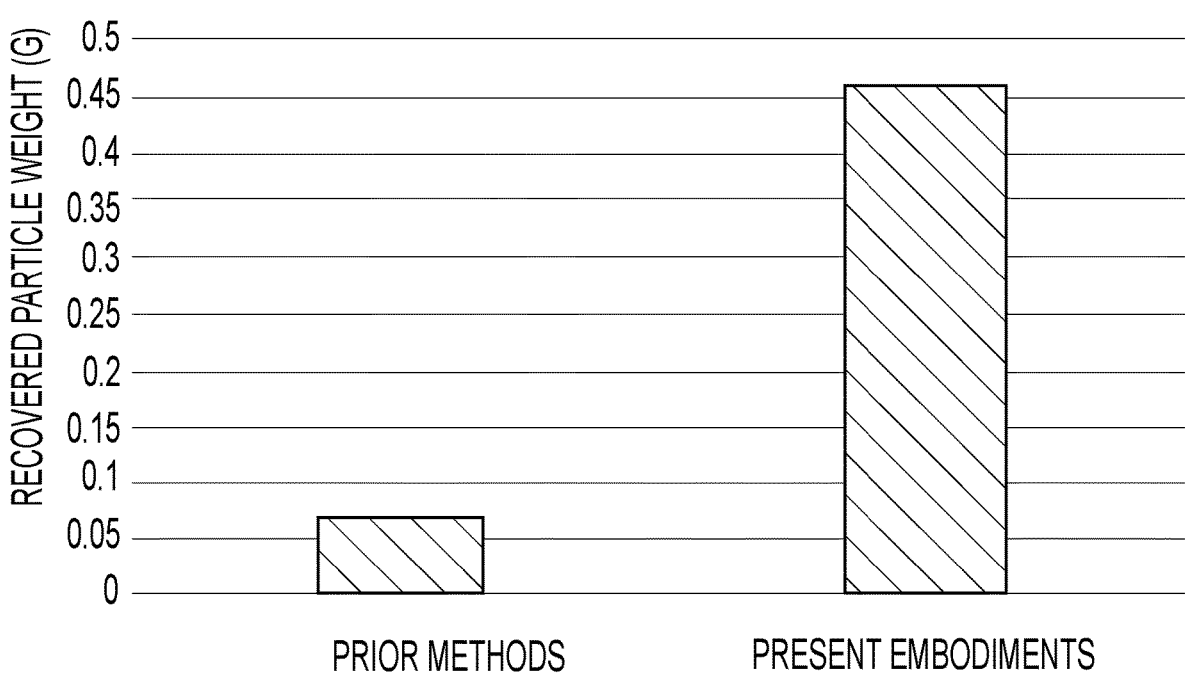
FIG. 4 is a graph showing the weight of recovered hydrogel particles using prior art methods compared to some embodiments of methods disclosed herein.

As mentioned above, method 100 significantly increases the yield of the hydrogel particles compared to prior art methods. For example, as illustrated in FIG. 4, prior art methods lacking the suspension media removal steps disclosed herein may have a yield of about 14% that of the methods disclosed herein. In these experiments, 0.15 grams of starting hydrogel material was used. Following separation, prior art methods yielded 0.064 grams of hydrogel particles while methods disclosed herein yielded 0.46 grams. The recovery weight includes added mass of water from the swollen hydrogel. Additionally, method 100 may be used to generate low to high levels of hydrogel particles containing encapsulated cargo. For example, in some embodiments method 100 may be used to generate between about 0.01 mg to about 1 g of hydrogel particles. In some embodiments, method 100 may be used to generate between about 1 g to about 10 g of hydrogel particles. In some embodiments, method 100 may be used to generate between about 10 g to about 1 kg of hydrogel particles.

Figure 5:
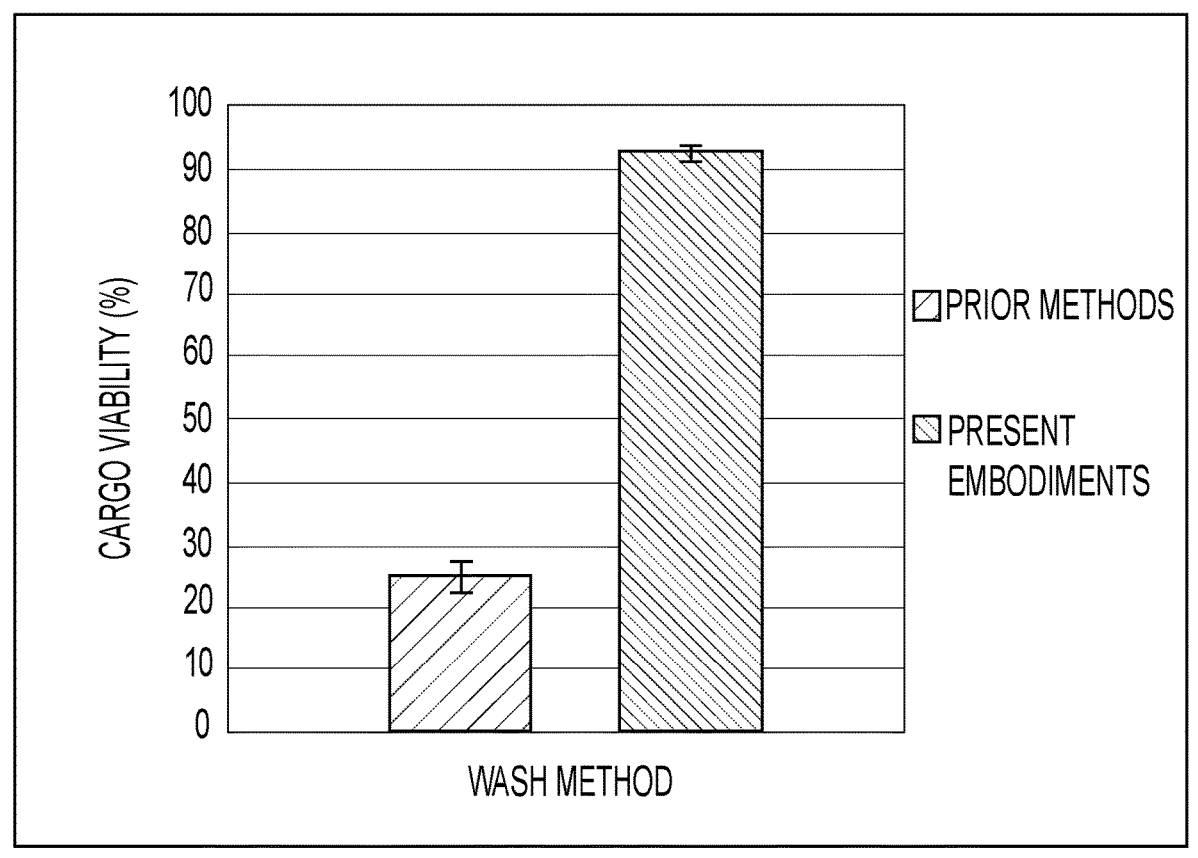
FIG. 5 is a graph showing viability of hydrogel cargo using prior art methods compared to some embodiments of methods disclosed herein.

As mentioned above, method 100 significantly increases the viability of the encapsulated cargo compared to prior methods. For example, as illustrated in FIG. 5, prior methods of suspension media removal from the hydrogel mixture may decrease cargo viability (e.g., cell viability) down to about 25% while methods disclosed herein maintain cargo viability at about 90% or greater (e.g., about 93%). Said another way, of the cargo mixture combined in step 141, only 25% of that cargo is viable following prior art purification techniques. In contrast, methods disclosed herein result in cargo viability (e.g., cell viability) of about 90% or greater (e.g., 93% cell viability). Error bars shown in FIG. 5 represent standard deviation based on four repetitions of encapsulating cells via each of the present and prior methods.

Automated Encapsulation of Viable Cells in Hydrogel Particles

FIG. 6 is a block diagram showing an exemplary automated encapsulation method 200. An automated method for encapsulating viable cells is desired to scale-up the process described above for GMP production, to reduce the chance of contamination, and to increase the total number of cells encapsulated for use with in vivo applications by employing continuous production ability. In embodiments disclosed herein, the automated encapsulation method 200 may be used for encapsulating viable equine MSCs in hydrogel particles; however, other types of viable mammalian cells may be encapsulated in hydrogel particles using method 200 without departing from the scope hereof.

In a step 210, mammalian cells are grown in a bioreactor. In an example of step 210, mammalian cells are grown in a bioreactor (e.g., a Thermo Fisher 500 L DynaDrive Single-Use Bioreactor) until a desired cell number is reached. The cells may be harvested between about 10% to 100% confluence. In some embodiments, the cells are harvested between about 70% to 80% confluence. Continuous monitoring of cell growth parameters may be automatically performed via an integrated sensor system.

In a step 220, mammalian cells are harvested automatically from the bioreactor. In an example of step 220, an automated centrifuge system that is connected to the bioreactor is used to automatically harvest the cells from the bioreactor. In embodiments, the automated cell harvest process follows the same centrifuging procedure as the manual operation described above in step 143 (e.g., spin at 7000 rpm for three minutes). The cells may then be resuspended from a cell pellet in media (e.g., DMEM, PBS, or other media type), and the centrifuging and resuspending steps may be repeated one or more times.

In a step 230, a cell suspension is adjusted to a desired cell concentration. In an example of step 230, an automated liquid handling system is used to count a sample of cells from a mammalian cell suspension for determining the cell concentration, and the automated liquid handling system then adds or removes media to achieve the desired cell concentration. An example automated liquid handling system is a Beckman Coulter integrated solution, incorporating an automated cell counting system such as Beckman Coulter Vi-CELL MetaFLEX.

In a step 240, hydrogel materials are combined with the cell suspension to form a hydrogel mixture. Step 240 is an automated example of step 110 described above. For example, an automated liquid handling system is programmed to measure and combine components of a cargo-compatible solution with a cargo suspension to generate the hydrogel mixture. The cargo-compatible solution may comprise a hydrogel polymer, a linker, a suspension media, and a surfactant. In embodiments, the cargo-compatible solution comprises one or more of PEGNB, DMEM, a linker (e.g. 3.5 Kilodalton PEG di-thiol linker), and LAP. In some embodiments, the automated liquid handling system is programmed to measure and mix the components of the cargo-compatible solution in a dark tube. The cargo-compatible solution may be prepared ahead of time in batches and stored until required (e.g., at 10° C. for one to seven days).

The cargo suspension comprises the cargo (e.g., cells) and a suspension media that is compatible with the cargo. In embodiments, the cargo suspension comprises the cell suspension from step 230 and the suspension media comprises an oil such as NOVEC™ 7500 oil (3M™) with fluorosurfactant or other analogous surfactant. The cell suspension and the suspension media are automatically combined via the liquid handling system.

In a step 245, the hydrogel mixture is mixed. Step 245 is an automated example of step 120 described above. In embodiments, the hydrogel mixture is automatically mixed with a shaking device programmed to shake at a speed of approximately three to five shakes per second and for a total of between five to seven shakes. In some embodiments, the hydrogel mixture is automatically mixed with a speed of approximately four shakes per second and the hydrogel mixture is automatically mixed for six shakes. Step 245 is configured to form an emulsion of hydrogel droplets.

In a step 250, the hydrogel mixture is polymerized. Step 250 is an automated example of step 130 described above. For example, using a robotic arm, the hydrogel mixture may be exposed to a UV light source, or near UV light source at a specific wavelength (e.g., 365-nm to 435-nm), a specific energy, and a specific time to cause polymerization of the hydrogel polymers contained within. In embodiments, tubes containing hydrogel mixture are transferred to an automated UV exposure device using the robotic arm. The automated UV exposure device may be programmed to irradiate the hydrogel mixture with UV light (e.g., at 100 mW/cm² for 20 seconds). Step 250 is configured to polymerize the hydrogel thereby trapping the cells within the droplets.

In a step 255, a surfactant solution of is prepared. In an example of step 255, the automated liquid handling system adds 10 μl of pluronic F68 surfactant to 1 ml media (final concentration of 0.1% F68). The surfactant may be added to wash media to help eliminate oil.

In a step 265, a density adjusting material is automatically added to the hydrogel-suspension media mixture. Step 265 is an example of step 141 described above, with the density adjusting material being added via the automated liquid handling system.

In a step 270, the hydrogel mixture is centrifuged. In an example of step 270, the automated liquid handling system adds Opti-prep and media containing surfactant (e.g., 0.1% F68) to the tubes, transfers the tubes to the centrifuge, and the mixture may be centrifuged for 3 minutes at a force of 350 rcf. Step 270 is an automated example of step 143 described above in which a three-phase solution is formed.

In a step 275, the mixture is automatically mechanically agitated. In an example of step 275, the robotic arm moves the tubes containing the hydrogel mixture to a mechanical mixing device (e.g., a Scientific Industries GENIE G560 Vortex-Genie 2) and mixes the hydrogel mixture using a force of about 1 Newton per 300 μl of particles about 20 times to dislodge the hydrogel/suspension media clump. Step 275 is an example of step 144 described above. For example, hydrogel/suspension media clumps are portions of hydrogel particles that are partially held together due to trapped suspension media held therebetween. The trapped suspension media not only causes the hydrogel particles to stick to one another, but the clumps may also stick to the side of the container. To sufficiently remove the suspension media from the hydrogel particles, the hydrogel/suspension media clumps may need to be dislodged from the side of the container. In some embodiments, a force of between about 0.5 Newtons to about 5000 Newtons is used to dislodge the hydrogel/suspension media clumps. In some embodiments, the mechanical agitation may be performed between about 3 times to about 40 times. Since step 275 is performed after the cargo has been encapsulated in the appropriately sized hydrogel particles, mechanical agitation may be used at this step without affecting the size of the particles and the amount of cargo encapsulated.

In an optional step 280, more density adjusting material may be added to the hydrogel mixture. Step 280 is an example of step 145 described above. Adding an additional layer of density adjusting material may aid in a final step of centrifugation to pull out any additional suspension media that may be leftover in the hydrogel phase.

In a step 285, the mixture is centrifuged for a final time to separate the suspension media from the hydrogel material. Step 285 is an example of step 146 described above in which the mixture is centrifuged at 350 rcf for 3 minutes.

In a step 290, the hydrogel particles are rinsed with media to remove any remaining oil and Opti-prep while avoiding the hydrogels from drying. In an example of step 290, the liquid handling system transfers the hydrogel particles to a filter via automated pipetting and rinses the hydrogels with appropriate media (e.g., PBS) via the liquid handling system.

In an optional step 295, the hydrogel particles are examined via an automated microscope to ensure correct encapsulation and substantially no clumping of particles. In an example of step 295, a microscope equipped with a digital camera captures images of the hydrogel particles and a sample of the particles are evaluated automatically via digital imaging software trained to determine correct encapsulation and substantially no clumping of particles. In embodiments, correct encapsulation comprises a mean particle size distribution within about one standard deviation from a desired diameter, and particles are distributed within a 10% error of training images demonstrating no clumping.

In a step 300, the hydrogel particles are retrieved and transferred for dispensing. In an example of step 300, the hydrogel particles are retrieved via the automated liquid handling system and transferred to a dispensing reservoir operably connected to an automated filling system. The automated filling system may be an Integrated Automated Filling Machine from the Filamatic Company, in some embodiments.

In a step 310, the automated filling system dispenses a predetermined amount of hydrogel particles into cryo-vials. In an example of step 310, hydrogel particles are dispensed in 1-mL aliquots into cryo-vials.

In a step 320, a cryoprotectant is added to each cryo-vial. In an example of step 320, 0.2-mL of proprietary Cryoprotectant is added via the automated liquid handling system to each of the cryo-vials. This step helps protect the encapsulated cells from damage during freezing for long-term storage.

In a step 330, a robotic arm is used to transfer the cryo-vials to a controlled-rate freezing device for cooling the encapsulated cells. In an example of step 330, the encapsulated cells are cooled at a predetermined rate via the controlled-rate freezing device (e.g., a Cytiva VIA Freeze Controlled-Rate Freezer) to freeze the hydrogel particles for storage.

In a step 340, cooled vials of encapsulated cells are transferred to a cryogenic storage system. In an example of step 340, cooled vials of encapsulated cells are transferred via the robotic arm to a cryogenic freezer (e.g., at −196° C.). In some embodiments, the cryogenic storage system is equipped with automated inventory tracking, which logs the details (e.g., contents, date, etc.) for facilitating later retrieval. Prior to use, frozen vials of encapsulated cells are thawed (e.g., via submersion and agitation in a 37° C. liquid bath for approximately 1 to 5 minutes).

Encapsulation of Cells at Commercial Throughput with High Long-Term Viability

Embodiments of the invention comprise a composition for orthopedic tissue rejuvenation via the hydrogel particle encapsulation and suspension media removal method 100 described above. The composition was used to regenerate tendon/ligament tissue using allogeneic, marrow-derived mesenchymal stem cells (MSCs) encapsulated in microscopic hydrogel droplets.

Figure 7:
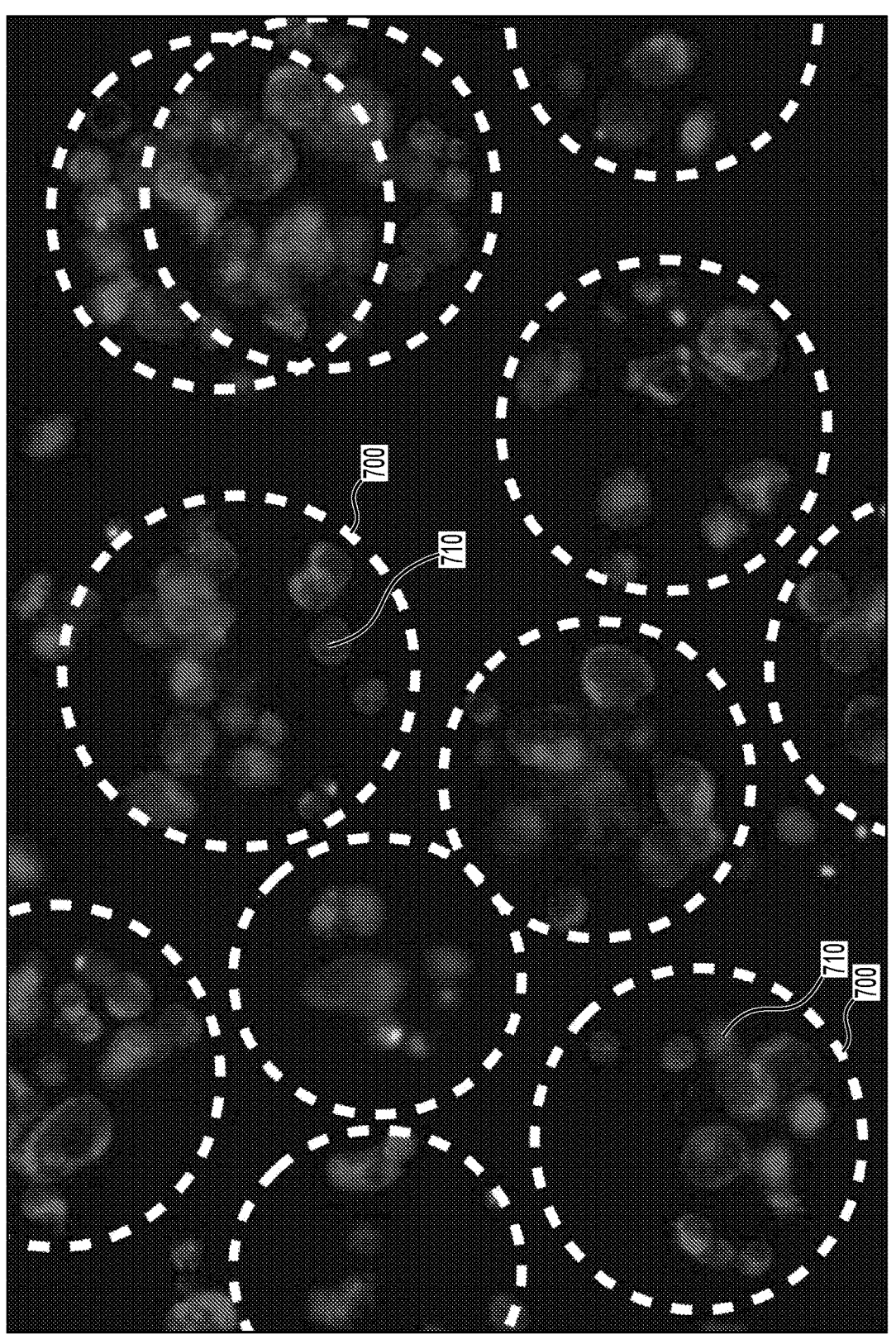
FIG. 7 shows an exemplary fluorescent microscope image of cells encapsulated in microscopic hydrogel droplets.

FIG. 7 shows an exemplary fluorescent microscope image of MSCs 710 encapsulated in spherical hydrogel droplets 700. The spherical droplets 700 are not directly visible in the image but are indicated in FIG. 7 with dashed lines. A diameter of the spherical droplets is from about 100 μm to about 300 μm. Image J is used to determine the diameter from images automatically.

Microscopic hydrogel droplets enable injection through a standard syringe. Example syringe sizes that may be used to inject the spherical hydrogel droplets formed via method 100 or method 200 described herein include a 14-gauge needle, a 16-gauge, a 21-gauge needle, and a 26-gauge needle. The small droplet size produced via methods 100/200 combined with the unique composition provides unhindered transport of nutrients, cytokines, and waste to and from the encapsulated cells. The "sticky" property of the hydrogel droplets keeps them localized at the injection site. After injection, the cells inside act like miniature bioreactors, signaling native cells to heal damaged tissue. In addition, the protective hydrogel shields encapsulated cells from immune detection, avoiding longstanding problems with allogeneic therapy.

Production scalability of this novel composition was investigated, along with its safety and efficacy in a rodent model of damaged Achilles tendon tissue.

Scalability studies involved producing hydrogel microencapsulated marrow derived MSCs at scale using method 100 described above. Cell viability, cell stemness, and safety of the composition was verified through characterization of stem cell behavior via gene expression analysis, yielding an optimum range for the number of cells encapsulated per droplet, and demonstrating that cells maintain genetic markers highly associated with non-differentiated "stem" like properties. This indicates that encapsulation does not cause unintentional and potentially deleterious cell differentiation, which would compromise therapeutic safety and/or efficacy. Further gene expression studies demonstrated a mechanism by which tendon regeneration may be influenced, indicating upregulation of the gene Gdf7, which is associated with tendon development and healing.

Results from rodent efficacy studies demonstrated that the hydrogel droplet delivery system disclosed herein keeps cargo localized at an injury site, with "sticky" droplets annealing to form a plug in the tendon defect and maintaining cargo in this plug for at least 5 days. Histology results demonstrated the composition induced regeneration of tissue with less hypercellularity, more aligned collagen, a more natural overall morphology, and a reduction in secondary inflammation. These findings are indicative of a reduction in undesirable scar tissue and overall better healing compared to current art.

The histology results were paired with gene expression analysis, the results of which demonstrate that hydrogel encapsulated cell treatments downregulate expression of scleraxis (SCX) and reduce the expression of vascular endothelial growth factor (VEGF) at a key timepoint in healing, suggesting regeneration with superior mechanical properties and a healthy inflammation response, respectively. Safety studies included examination of the kidneys and spleens of all animals by a board-certified pathologist, and no signs of toxicity were found. These results strongly indicate that this novel composition is safe, and that it supports more durable healing leading to a reduced likelihood of reinjury. The results also confirm that the Hydrogel Encapsulation and Suspension Media Removal Method used for producing this composition does not adversely impact function.

Cell viability and stem cell-like behavior are both necessary to facilitate safe and effective regeneration of damaged tissue. In this objective, the following technical tasks were performed to quantitively assess metrics of cell viability and stem cell-like behavior for the encapsulated cells formed via method 200 compared with baseline unencapsulated cell metrics.

Methods: As described above in step 210, MSCs isolated from rat and horse bone marrow were cultured in DMEM (Sigma) (low glucose) supplemented with 15% FBS (Sigma) and penicillin/streptomycin (Sigma). As described above in step 220, MSCs at approximately 80% confluency were dissociated from the culture flask with Accutase (Sigma) for 10 min at room temperature. As described above in step 230, the MSCs were adjusted to a desired cell concentration (e.g., $10^8$ cells/ml). As described above in step 240, a hydrogel solution (100 μl) was prepared containing 10% (w/v) PEG-NB (Creative PEG-Works), 0.1% LAP (Sigma) (w/v), 10 mM of PEG dithiol (Creative PEG-Works) (3.5K Dalton), and $10^7$ MSCs. This hydrogel/cell mixture was then laid on top of 300 μl NOVEC fluid (3M) in a 1.5-ml tube. Encapsulated MSCs in hydrogel particles were generated via an emulsion technique described above in step 245 for shaking the hydrogel mixture followed by UV-induced polymerization (step 250). Suspension media removal, described above in steps 255 to 290, was used to purify encapsulated cells, which were then seeded into a 96-well plate so that wells contained monolayers of particles. The encapsulated MSCs were cultured over 14 days. On specific days, multiple wells were stained with LIVE/DEAD™ assay dye (Thermo Fisher) to determine the number of live and dead cells. The total number of cells per well was determined by a cell tracker dye and automated fluorescence microscopy as described above in step 295. Viability (%) was determined by dividing the number of live cells by the total number of cells per well. The encapsulated MSCs were retrieved as described above in step 300.

Figure 8:
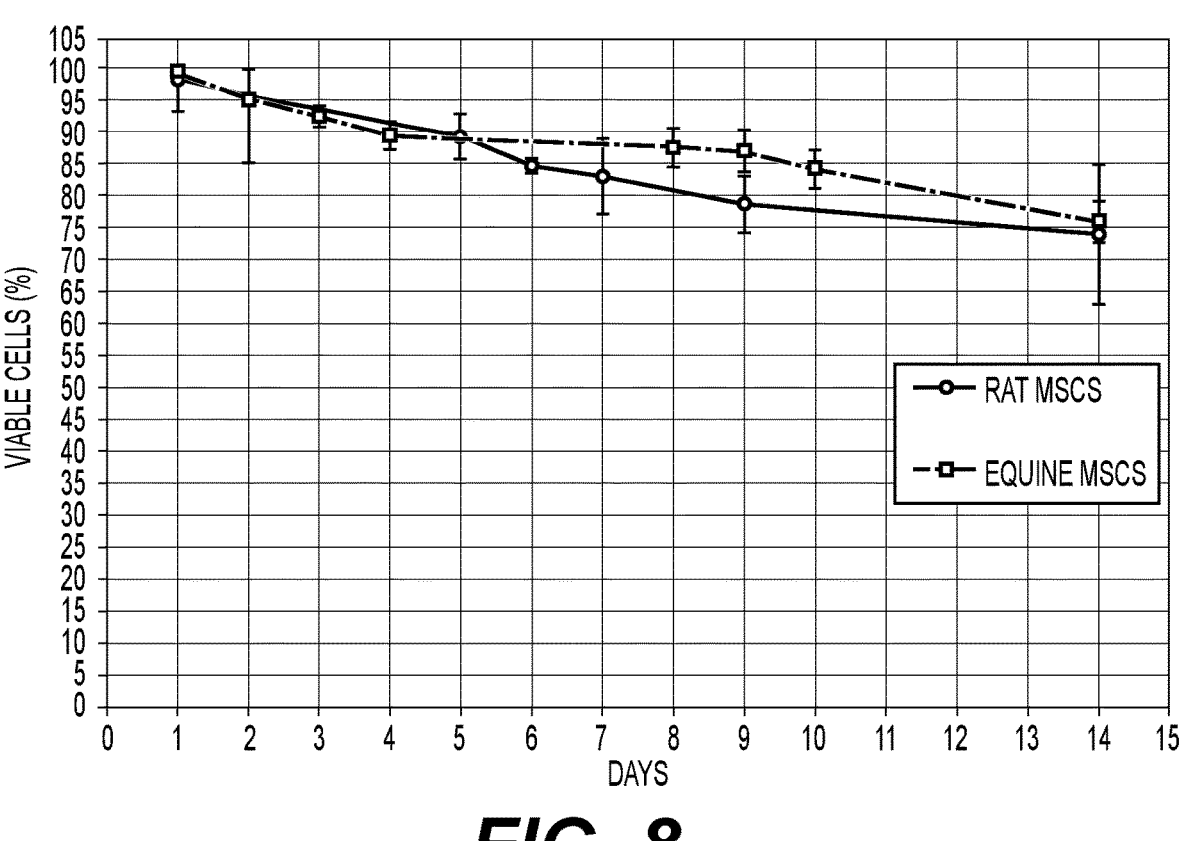
FIG. 8 shows cell viability of rat and equine encapsulated mesenchymal stem cells (MSCs) over time.

Results: Rat MSCs encapsulated via the automated encapsulation method 100 were capable of meeting commercial production and maintained a viability of 74.4% after 14 days in culture (FIG. 8). The viability of encapsulated horse MSCs intended for use in equine stem cell therapy was also assessed using the same protocol. We found that equine MSCs maintain a viability of 85% after 10 days, and 76% after 2 weeks (FIG. 8), demonstrating an excellent response to this commercial-scale hydrogel microencapsulation method. Of note is the response of cell viability to encapsulated cell number, where more than approximately 50 cells encapsulated withing an approximately 300 µm diameter droplet triggers cell apoptosis over a 24 h period after encapsulation. An optimum quantity of cells per droplet for maximum viability while maintaining therapeutic efficacy was determined based on this.

Analyze Markers of Stemness in Encapsulated Cells

Unintended differentiation of MSCs during encapsulation could produce deleterious results or reduce therapeutic efficacy. Expression of CD29 and CD44 genes, coupled with low expression of CD45, is a highly conserved pattern across stem-like cells (those capable of differentiating into multiple lineages). Testing for this expression pattern provides evidence that encapsulation does not induce equine MSC differentiation. Expression of CD29 and CD44 genes varies naturally between stem-like cells due to factors such as age, passage number, etc. For this reason, a broad range of acceptable expression levels over the trial period was selected. CD45 gene expression should not show a statistically significant increase over the time period.

Methods: As described above using the automated encapsulation method 200, rat MSCs were encapsulated in hydrogel at a density of $10^7$ cells/ml. The MSCs were cultured in a 6-well plate and collected on the 7th and 14th days. Two wells of encapsulated cells in the 6-well plate were collected at each time point and processed for RNA purification, using the RNAeasy kit from Qiagen. Cells immediately after encapsulation served as a "Day 0" control. Quantitative PCR was performed using total RNA (2 ng) as input in a one-step RT-qPCR method. Expression was measured using the comparative Ct ($\Delta\Delta$Ct) method. The housekeeping gene Hprt was used as an internal control.

In addition to the above gene expression analysis, the expression of Gdf7 was measured in encapsulated cells over a 1-week period. Gdf7 encodes for a protein in the TGF-$\beta$ family. It plays a role in the differentiation of tendon cells during embryonic development and healing. Thus, it was of interest as to whether encapsulation of MSCs in a 3D matrix could influence its expression.

Results: Relative expression among genes was determined by Ct values, where one Ct difference equals an approximately 2-fold change in copy number. Stem cell-specific markers CD29 and CD44 were detected in encapsulated MSCs, and their expression increased modestly on day 7 and day 14 (FIG. 9A). CD45, a marker not associated with stem cells, was near the limit of detection on all days (FIG. 9A). In FIG. 9B, the expression of CD29, CD44, and CD45 is shown normalized to the reference gene Hprt. Over the 14-day period, CD45 expression increased slightly on day 7 and then decreased on day 14 compared to day 0. CD45 expression was less than 0.001% of reference gene expression on all days. The absence of significant CD45 expression, coupled with strong levels of CD29 and CD44 expression over the 14-day period, indicates that encapsulated MSCs retain characteristic stem cell properties throughout this time period.

FIG. 10 shows that encapsulation in hydrogel droplets via method 200 significantly increased Gdf7 expression in bone marrow-derived rat MSCs. To be certain these results were not anomalous, the experiment was repeated and similar results were obtained. It may be that the hydrogel properties and encapsulation process influence this behavior. Of interest is that although MSCs expressed this gene, they did not differentiate, as evidenced by the above results (FIGS. 9A and 9B).

Localize Droplet Cargo in a Rat Achilles Tendon Defect

Short retention times and poor viability of MSCs after injection into injured tissue are major issues that limit the effectiveness of regenerative cellular therapies. The myriad of inflammatory and immunogenic factors present in vivo are not easily replicated in vitro.

The following tasks were completed to provide evidence that hydrogel droplets are localized at the injury site in vivo, are nontoxic and non-immunogenic, and exhibit markers of superior tissue regeneration in vivo.

To test the ability of hydrogel droplets to localize cargo at an injury site, 10-µm diameter fluorescein-5-isothiocyanate (FITC) fluorescent beads were encapsulated in hydrogel droplets and injected into wounded rat Achilles tendons. This was compared to non-encapsulated FITC beads injected into the wound site. A 1.5-mm surgical punch injury was created in the right Achilles tendons of four Sprague-Dawley rats, the wound site sutured, and 2 days later three animals were injected with 75 µl of hydrogel droplets in phosphate-buffered saline (PBS) at a density of $1\times10^7$ beads/mL. The remaining animal was injected with 75 µl of non-encapsulated FITC beads at a density of $1\times10^7$ beads/mL. One rat containing droplet encapsulated beads was sacrificed according to the IACUC-approved protocol 24 hours after injection, and the rest were sacrificed 5 days after injection. The Achilles tendons of all animals were dissected out and imaged under a brightfield microscope.

Results: FIG. 11A shows the 10-µm FITC fluorescent beads encapsulated in hydrogel droplets sticking to the surface of an Achilles tendon 24 hours after injection. The droplets appeared to have "sticky" properties, helping them adhere to tissue. FIG. 11B shows the hydrogel-encapsulated FITC fluorescent beads 5 days after injection. The hydrogel droplets annealed together inside the punch wound (indicated by the dashed line in FIG. 11B), creating a plug. As shown in FIG. 11C, no such retention of fluorescent beads was seen in the punch wound (indicated by the dashed line in FIG. 11C) 5 days after treatment with non-encapsulated FITC fluorescent beads, as depicted. These results suggest that the composition sticks to tissue, localizing cargo at an injury site for at least 5 days, and creating a scaffold potentially amenable to tissue regeneration. In contrast, beads lacking the hydrogel carrier were not retained at the injury site, providing preliminary evidence for the benefits of the novel composition.

Assess Immunogenicity of Hydrogel Encapsulated MSC Injection

Methods: To determine if the composition induced an unwanted immune response, immunohistochemistry was used to selectively label inflammatory M1 macrophages in Achilles tendon tissue across four experimental groups: 1) hydrogel droplet-encapsulated allogeneic Sprague Dawley rat MSCs, 2) non-encapsulated allogeneic Sprague Dawley rat MSCs, 3) hydrogel droplets, and 4) PBS injection control. Cells were encapsulated in droplets at a density of $10^7$ cells/mL and prepared at a final concentration of $5\times10^6$ cells/mL for encapsulated and non-encapsulated injections. The final concentration may range from about $5\times10^5$ cells/mL to about $5\times10^7$ cells/mL without departing from the scope hereof. An equivalent droplet density was used for both the hydrogel droplet-encapsulated cell group and "empty" hydrogel droplet carrier group. A 75-µl injection volume was used for all experimental groups. However, in practice a volume of the hydrogel droplet composition is about 0.05 mL to about 10 mL for administering in vivo. Prior to administering injections, the injury site may be imaged by one or a combination of X-ray, ultrasound, or MRI, for example. Live imaging (e.g., via ultrasound) may be used to help guide injections to the injury site.

Surgeries to the right Achilles tendon were carried out on 12 animals as described above. Two days after surgery, the Achilles injury sites were treated according to the above experimental groups (n=3 animals/group). Five days after injection, animals were sacrificed and the Achilles tendon of each animal dissected out and cut in half down the transverse plane though the center of the punch injury. One half of the tendon was preserved for gene analysis, and the other half imbedded in Optimal Cutting Temperature (OTC) compound, sectioned through the transverse plane at the defect site, and immunohistochemically labeled for M1 macrophage infiltration using CD86 antibody (Thermo Fisher Scientific, Inc.) and a FITC-tagged secondary antibody (Thermo Fisher Scientific, Inc.). Sections were imaged via fluorescent microscopy, and the mean grey value of the entire section was assessed using ImageJ to quantify the fluorescent intensity. The results are scaled to surface area.

Results: FIG. 12 indicates that the composition did not lead to an increase in M1 macrophages, which otherwise would have be expected with an elevated immune response. Naked stem cells demonstrated a slight elevation in M1 macrophages compared to the other cohorts, which was reduced by encapsulation in hydrogel. However, this effect was not statistically significant. The lack of a statistically significant elevation in M1 macrophages over PBS control for both the novel composition and empty hydrogel droplets demonstrates that the composition is non-immunogenetic, which provides evidence of its safety and efficacy.

Assess Histological Markers of Tendon Tissue Regeneration

Methods: Histological evaluation of tissue regeneration provides important evidence of efficacy between the experimental groups. To assess endpoint healing outcomes, 9 Sprague Dawley rats were administered surgical defects in their right Achilles tendons as described above. Two days later, animals were randomized into the following treatment groups (n=3 animals/group): 1) hydrogel encapsulated MSCs, 2) non-encapsulated MSCs, and 3) PBS as described in above. 28 days later, animals were euthanized, both hindlimbs removed, the Achilles tendons exposed, and both limbs immediately fixed in 4% paraformaldehyde (Sigma), with the left Achilles from each animal serving as a control. Tendons from all limbs were then dissected out, paraffin embedded, sectioned, and stained with Alcian blue (EMS) and hematoxylin and eosin (H&E) (EMS). Slides were imaged via slide scanner, results read and scored by a board-certified pathologist, and tissue analyzed via Qu-path software.

Results: Representative images from H&E-EMS stained sections are shown in FIGS. 13A-13D. FIG. 13A shows a healthy Achilles tendon; FIG. 13B shows the encapsulated MSC-treated Achilles tendon; FIG. 13C shows naked (non-encapsulated) MSC-treated Achilles tendon; and FIG. 13D shows PBS-treated Achilles tendon. The encapsulated MSC-treated cohort (as shown in FIG. 13B) demonstrated less hypercellularity of regenerated tissue (more pink vs. purple), greater collagen alignment, and an overall Achilles morphology more similar to that of the healthy non-injured tendon (FIG. 13A). These indicators of desirable healing suggest improved function and durability of the composition treated cohort over non-encapsulated MSCs and PBS control. Quantitative assessments of tissue regeneration were made via Bonar scoring and comparative measurement of the area of healthy tendon tissue (pink) to hypercellular tissue (purple) in each sample. Bonar scoring was used to numerically assess metrics of tenocyte morphology, ground substance (mucin), collagen alignment, and vascularity for the location of greatest pathology observed in each tendon. A 500 μm×500 μm section was scored.

FIG. 14A is an illustration of rat Achilles tendon morphology showing calcaneus (Cal), soleus (Sol), lateral gastrocnemius (Lg), and medial gastrocnemius (Mg) muscles. FIG. 14B shows a healthy Achilles tendon; FIG. 14C shows the encapsulated MSC-treated injured Achilles tendon; and FIG. 14D shows the PBS-treated injured Achilles tendon. The Achilles tendon treated with the encapsulated MSC (FIG. 14C) is more similar in size and morphology to the healthy Achilles tendon FIG. 14B than the untreated (PBS control) Achilles tendon (FIG. 14D).

FIG. 15 shows the average Bonar score over the four scored metrics for each experimental group. Scoring did not indicate a statistically significant difference between groups. A notable consideration to this result is that scoring was conducted over a select area picked as the most pathologically affected and did not take into account the total tendon. Although the original wound was a 1.5-mm diameter circular punch, the tendons demonstrated pathology not localized to a single area. This is hypothesized to be from secondary tendinopathy triggered by immune response from the initial injury.

To better capture the health of the entire tendon, the ratio of healthy to pathologic tissue was measured across its entirety. Comparative areas of tissue were measured via Qu-Path software using the morphology of the uninjured control to select tissue with analogous characteristics, e.g. pink coloration indicating absence of hypercellularity, aligned collagen fibrils, and absence of mucin stain compared to areas of purple coloration indicating hypercellularity, misaligned collagen, and background mucin stain, all indicative of pathology. The MSC-encapsulated treated cohort was associated with a significant increase in the amount of healthy tendon tissue compared to the non-encapsulated MSC and PBS injection groups (FIG. 16), with an average of 25% more healthy tendon tissue compared to the non-encapsulated MSC treatment cohort. The novel composition treated cohort also demonstrated overall tendon structure most similar to that of the healthy control. Unlike both the non-encapsulated cell and PBS injection cohorts, animals treated with encapsulated MSCs exhibited the three distinct tendon bundles that comprise the Achilles (FIG. 14C), as well as significantly less inflammation of the peritenon (FIG. 17). Inflammation of the peritenon sheath, or paratenonitis, is a pathology causing tendon pain and indicates progress to overall tendinopathy. As shown in FIG. 17, both encapsulated and non-encapsulated treatment cohorts had similar Achilles tendon diameters 7 days after injury, and both were significantly smaller than the tendons of the PBS injection cohort. At 28 days after injury, the encapsulated cell cohort exhibited a further decrease in diameter, restoring it to a diameter that was approximately equivalent to that of the healthy control, while the non-encapsulated and PBS treatment cohorts exhibited continued increases in diameter.

Together, the greater quantity of healthy tissue, less aberrant overall Achilles structure, and less inflammation of the peritenon suggest that the novel composition elicited a beneficial effect on healing, in part by mitigating the development of secondary tendinopathies. This evidence is also supported by results demonstrating upregulation of Gdf7 gene expression in encapsulated MSCs (discussed above), and downregulation of SCX and VEGF gene expressions in tendon tissue taken from the encapsulated cell-treated group, discussed below.

Assess Genetic Markers of Tendon Tissue Regeneration

Methods: Gene expression was conducted on day 7 after surgery, near the end of the inflammatory stage, and beginning of the proliferative phase of tendon healing. The rationale behind choosing this timepoint was to probe SCX expression, which is known to be elevated during the inflammatory stage, as well as to probe differences in inflammation that may be more apparent at this crossover point.

Achilles punch surgeries were conducted as above, with a second half of the Achilles being placed in ZYMO DNA/RNA stabilizer solution for later genetic analysis. A 3-mm cube of tissue immediately adjacent to the punch location was removed for RNA isolation, and individual tissue specimens were frozen in liquid nitrogen and ground into powder. Lysis buffer was then added (Thermos Fisher Scientific, Inc.), and total RNA was isolated using the Qiagen RNeasy kit. Quantitative PCR was performed using total RNA (2 ng) as input in a one-step RT-qPCR method. Expression was measured using the comparative Ct ($\Delta\Delta$Ct) method. The housekeeping gene Hprt was used as an internal control.

Results: FIGS. 18-19 show gene expression analysis results for SCX and VEGF-A, respectively. SCX is an important regulator of tendon development, and previous work has demonstrated that limiting its expression during healing is correlated with improved tendon strength and tissue quality. VEGF-A plays a role in healing by inducing the growth of blood-carrying vessels to injured tissue. Although it plays a crucial role in the initial inflammation stage of healing, continued expression is implicated in pathologic responses to tendon injury, causing long-term inflammation associated with tendinopathy.

As shown in FIG. 18, both injections of the non-encapsulated MSCs and novel composition of encapsulated MSCs (formed using method 200) downregulated the expression of SCX in tendon tissue compared to the hydrogel droplet formed with PEGNB(NB) and PBS controls. All injured groups showed upregulated expression over that of the healthy control, which is expected as it is a gene activated during the inflammation phase of healing. The downregulation of SCX in both cell injection cohorts indicates that MSCs may modulate expression of this gene, contributing to better healing outcomes according to the literature.

FIG. 19 shows that the encapsulated MSC treatment cohort exhibited reduced expression of VEGF-A in tendon tissue compared to the non-encapsulated MSC cohort. Similar VEGF-A expression levels are seen in the hydrogel droplet, PBS injection, and encapsulated MSC cohorts. All three showed reduced expression compared to the healthy control. This is expected given the point selected in the healing process (i.e., the transition from the inflammation phase to the proliferative phase). Previously upregulated expression should drop to below base levels, turning off vascularization and its associated immune response.

Because VEGF-A expression should be upregulated during the inflammation phase of healing but not persist past this phase, the difference in expression levels between encapsulated and non-encapsulated cell cohorts may arise from the initial injection of "naked" allogeneic MSCs interacting with immune cells to dysregulate the healing cycle. The encapsulation of MSCs could prevent triggering such a response by shielding them from immune cells while maintaining their beneficial healing effects, such as the reduction in SCX expression. This is supported by signs of reduced inflammation and more quality tendon tissue according to histology in the novel composition treated cohort compared to the other cohorts. This information suggests another interesting benefit of the composition, whereby encapsulation of allogeneic cells via methods 100 and 200 lessens or prevents an otherwise deleterious immune response by shielding them from immune cell interaction.

Assess the Toxicity of Hydrogel-Encapsulated MSCs

Methods: To assess potential systemic effects of the encapsulated MSCs composition formed using method 100 or 200, and thereby determine its safety, the kidneys and spleens of animals from the immunogenicity assessment described above were collected and immediately preserved in 4% paraformaldehyde (Sigma) for later toxicology assessment. A licensed, board-certified pathologist analyzed the kidney and spleen samples in triplicate for any signs of toxicity 28 days after treatment with the novel composition, naked MSCs, or PBS control injections.

Results: Images from pathology are shown in FIG. 20A from spleen and FIG. 20B from kidney. The pathology report indicated that the kidneys showed only acute passive congestion, a consequence of permortem perfusion changes and a common finding that was not indicative of any disease. The spleen sections were also unremarkable with the possible exception of a single, non-hydrogel-treated sample, which had some early geminal center formation. The pathologist noted a slight response, but that this was not indicative of any pathology suggest preliminary safety in a rodent model.

High cell viability and the absence of aberrant cell behavior are both necessary to facilitate hydrogel encapsulated cell potency, which is paramount for safe and effective rejuvenation of damaged tissue. Prior art has been unable to reliably facilitate this due to poor cargo viability and harsh conditions impacting cell function, for example, encapsulated stem cells with low viability that lack markers of "stemness" arising from damage during the encapsulation process. The processes disclosed herein, namely using the hydrogel particle encapsulation and suspension media removal method 100 and the automated encapsulation method 200 described above, enables production of hydrogel encapsulated cargo (e.g., therapeutic cells) at sufficient quantities, purity, and therapeutic activities for high in vivo potency. This directly enables the formulation of novel, high potency compositions such as for the rejuvenation of orthopedic tissue, including a composition for tendon and ligament regeneration. Rodent results demonstrated strong preliminary evidence that methods 100 and 200 enable production of a novel composition of hydrogel droplet encapsulated marrow derived MSCs. This composition demonstrated the ability to induce superior tissue regeneration in animals, while also possessing a strong safety profile.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A hydrogel composition for orthopedic tissue rejuvenation, the hydrogel composition comprising:

a biologically compatible hydrogel suspension having hydrogel particles containing viable cells, wherein the hydrogel particles comprise:

a PEG norbornene-based hydrogel polymer;

the hydrogel polymer lacks cell-adhesive peptide groups; and wherein the hydrogel particles comprise spherical droplets having a diameter of about 100 μm to about 300 μm;

wherein the hydrogel particles contain a total number of cells between about 15 cells to about 50 cells per hydrogel particle;

wherein the viable cells within the hydrogel particles comprise an average viability of about 90% or greater; and wherein the biologically compatible suspension of hydrogel particles is devoid of suspension medium, such that the viable cells maintain viability of at least about 80% after 10 days and at least about 75% after two weeks.

2. The composition of claim 1, wherein the viable cells have an average viability of about 93% or greater.

3. The composition of claim 1, wherein the diameter of the spherical droplets is small enough to pass through a 16-gauge to a 21-gauge syringe typically used for orthopedic injection applications.

4. The composition of claim 1, wherein the viable cells are marrow-derived mesenchymal stem cells.

5. The composition of claim 4, wherein the marrow-derived mesenchymal stem cells retain stem-cell like properties within the hydrogel particles.

6. The composition of claim 5, wherein stem cell-specific markers CD29 and CD44 were expressed in the composition over at least a 14 day period, and CD45 was not expressed during the 14 day period, thereby indicating retainment of the stem-cell like properties over the 14 day period.

\*   \*   \*   \*   \*